(12) United States Patent
Ferrie et al.

(10) Patent No.: US 10,319,502 B2
(45) Date of Patent: Jun. 11, 2019

(54) POLYMER-ENCAPSULATED MAGNETIC NANOPARTICLES

(71) Applicant: CORNING INCORPORATED, Corning, NY (US)

(72) Inventors: Ann MeeJin Ferrie, Painted Post, NY (US); Yan Jin, Sunnyvale, CA (US); Lingyan Wang, Horseheads, NY (US); Yue Zhou, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 15/520,581

(22) PCT Filed: Oct. 23, 2015

(86) PCT No.: PCT/US2015/057036
§ 371 (c)(1),
(2) Date: Apr. 20, 2017

(87) PCT Pub. No.: WO2016/065218
PCT Pub. Date: Apr. 28, 2016

(65) Prior Publication Data
US 2018/0151278 A1    May 31, 2018

Related U.S. Application Data

(60) Provisional application No. 62/067,634, filed on Oct. 23, 2014.

(51) Int. Cl.
*H01F 1/12*  (2006.01)
*H01F 1/00*  (2006.01)
(Continued)

(52) U.S. Cl.
CPC ........... *H01F 1/12* (2013.01); *C12N 15/1013* (2013.01); *H01F 1/0054* (2013.01); *H01F 1/20* (2013.01); *H01F 1/344* (2013.01); *H01F 1/36* (2013.01)

(58) Field of Classification Search
CPC . H01F 1/0054; H01F 1/12; H01F 1/20; H01F 1/344; H01F 1/36
See application file for complete search history.

(56) References Cited

U.S. PATENT DOCUMENTS 4,459,378 A    7/1984  Ugelstad
4,530,956 A    7/1985  Ugelstad et al.
(Continued)

FOREIGN PATENT DOCUMENTS

CN    101417822 A    4/2009
CN    101707109 B   10/2011
(Continued)

OTHER PUBLICATIONS

Beneke, C. et al., "Polymeric Plant-Derived Excipients in Drug Delivery." Molecules, vol. 14, pp. 2602-2620, Jul. 16, 2009.
(Continued)

*Primary Examiner* — Alexandre F Ferre
(74) *Attorney, Agent, or Firm* — Frank Brock Riggs

(57) ABSTRACT

Magnetic particles (100) have a particle size (134) of 500 nm or less and include a core (110) and a polymer coating (120) that surrounds and encapsulates the core (110). The core (110) includes a metal, metal alloy, or metal oxide of at least one metal such as B, Mg, Al, Mn, Co, Ni, Cu, Fe Sm, Yb, Dy, Gd or Er and Nb. The magnetic core (100) is a polycrystalline particle and is a superspin glass magnetic material, having a coercivity greater than zero and a magnetic remanence greater than zero at room temperature. Above room temperature and at low field, the magnetic
(Continued)

moment of these superspin glass magnetic materials increases with temperature. An in situ hydrolysis/precipitation method from precursor metal salts is used to form the polymer-encapsulated magnetic particles (100).

11 Claims, 14 Drawing Sheets

(51) Int. Cl.
  *C12N 15/10* (2006.01)
  *H01F 1/34* (2006.01)
  *H01F 1/36* (2006.01)
  *H01F 1/20* (2006.01)

(56) References Cited

U.S. PATENT DOCUMENTS

| | | | |
|---|---|---|---|
| 5,130,423 | A | 7/1992 | Van Ness et al. |
| 5,459,378 | A | 10/1995 | Kato et al. |
| 5,523,231 | A | 6/1996 | Reeve |
| 5,648,124 | A | 7/1997 | Sutor |
| 5,681,946 | A | 10/1997 | Reeve |
| 5,695,900 | A | 12/1997 | Selim |
| 5,705,628 | A | 1/1998 | Hawkins |
| 5,898,071 | A | 4/1999 | Hawkins |
| 5,973,138 | A | 10/1999 | Collis |
| 5,990,302 | A | 11/1999 | Kuroita et al. |
| 6,423,296 | B1 | 7/2002 | Gunther et al. |
| 6,514,688 | B2 | 2/2003 | Muller-Schulte |
| 6,534,262 | B1 | 3/2003 | McKernan et al. |
| 6,562,573 | B2 | 5/2003 | Halaka |
| 6,649,414 | B1 | 11/2003 | Chandler et al. |
| 6,673,631 | B1 | 1/2004 | Tereba et al. |
| 6,773,812 | B2 | 8/2004 | Chandler et al. |
| 6,787,307 | B1 | 9/2004 | Bitner et al. |
| 6,914,137 | B2 | 7/2005 | Baker |
| 7,052,840 | B2 | 5/2006 | Carey et al. |
| 7,141,431 | B2 | 11/2006 | Chandler et al. |
| 7,208,271 | B2 | 4/2007 | Bost et al. |
| 7,329,491 | B2 | 2/2008 | Kirchgesser et al. |
| 7,491,495 | B2 | 2/2009 | Zielenski et al. |
| 7,537,898 | B2 | 5/2009 | Bost et al. |
| 7,560,160 | B2 | 7/2009 | Sudarshan et al. |
| 7,718,262 | B2 | 5/2010 | Chandler et al. |
| 7,754,278 | B2 | 7/2010 | Lee et al. |
| 7,785,660 | B2 | 8/2010 | Skagestad et al. |
| 7,977,109 | B2 | 7/2011 | Ritt et al. |
| 7,989,065 | B2 | 8/2011 | Winstead et al. |
| 8,029,991 | B2 | 10/2011 | Hillebrand |
| 8,129,118 | B2 | 3/2012 | Weindel et al. |
| 8,142,892 | B2 | 3/2012 | Rida |
| 8,283,037 | B2 | 10/2012 | Chandler et al. |
| 8,288,169 | B2 | 10/2012 | Utermohlen et al. |
| 8,420,055 | B2 | 4/2013 | Gaw et al. |
| 8,420,801 | B2 | 4/2013 | Johnson et al. |
| 8,426,126 | B2 | 4/2013 | Latham et al. |
| 8,507,198 | B2 | 8/2013 | Bost et al. |
| 8,636,906 | B2 | 1/2014 | Stein |
| 8,679,741 | B2 | 3/2014 | Hoyal-Wrightson et al. |
| 8,679,857 | B2 | 3/2014 | Suh et al. |
| 8,945,628 | B2 | 2/2015 | Weissleder et al. |
| 9,102,935 | B2 | 8/2015 | Erbacher et al. |
| 9,340,828 | B2 | 5/2016 | Estmer Nilsson et al. |
| 9,371,524 | B2 | 6/2016 | Will |
| 9,446,150 | B2 | 9/2016 | Lanza et al. |
| 9,617,534 | B2 | 4/2017 | Hennig et al. |
| 2005/0027040 | A1 | 2/2005 | Nelson et al. |
| 2006/0188876 | A1 | 8/2006 | Kilaas et al. |
| 2006/0286379 | A1 | 12/2006 | Gao |
| 2007/0172426 | A1 | 7/2007 | Lee et al. |
| 2009/0194733 | A1 | 8/2009 | Schulz et al. |
| 2009/0234112 | A1 | 9/2009 | Hillebrand |
| 2011/0160446 | A1 | 6/2011 | Ritt et al. |
| 2012/0245337 | A1 | 9/2012 | Fabis et al. |
| 2012/0305491 | A1 | 12/2012 | Ghandi |
| 2013/0112605 | A1 | 5/2013 | Wyndham et al. |
| 2014/0199689 | A1 | 7/2014 | Voss |
| 2014/0227712 | A1 | 8/2014 | Horlitz et al. |
| 2015/0125533 | A1 | 5/2015 | Sallam et al. |
| 2015/0218653 | A1 | 8/2015 | Sprenger-Haussels et al. |
| 2016/0281078 | A1 | 9/2016 | Fabis et al. |

FOREIGN PATENT DOCUMENTS

| | | |
|---|---|---|
| CN | 101935646 B | 7/2012 |
| CN | 102120168 B | 5/2013 |
| CN | 102552942 B | 6/2013 |
| CN | 103665278 A | 3/2014 |
| CN | 104120256 A | 10/2014 |
| CN | 102533724 B | 1/2016 |
| EP | 2244268 B1 | 4/2016 |
| WO | 1998012717 A1 | 3/1998 |
| WO | 2011099941 A1 | 8/2011 |

OTHER PUBLICATIONS

Elaissari A et al., "Hydrophilic Magnetic Latex for Nucleic Acid Extraction, Purification and Concentration." Journal of Magnetism and Magnetic Materials, vol. 225, pp. 127-133, Apr. 12, 2001.
Goon, I. et al., "Fabrication and Dispersion of Gold-Shell-Protected Magnetite Nanoparticles: Systematic Control Using Polyethyleneimine." Chemistry of Materials, vol. 21, No. 4, pp. 673-981, Jan. 22, 2009.
International Search Report and Written Opinion of the International Searching Authority; PCT/US2015/057036; dated Feb. 8, 2016; 11 Pages; European Patent Office.
Jiang, H. et al., "Superparamagnetic Core-Shell Structured Microspheres Carrying Carboxyl Groups as Adsorbents for Purification of Genomic DNA." Colloids and Surfaces A: Physicochemical and Engineering Aspects, vol. 401, pp. 74-80, Mar. 21, 2012.
Levison, P. et al, "Recent Developments of Magnetic Beads for Use in Nucleic Acid Purification." Journal of Chromatography A, vol. 816, Issue 1, pp. 107-111, Aug. 7, 1998.
Guo, M. et al., "Preparation and Characterization of Magnetic Poly(Epsilon-Caprolactone)-Poly(Ethylene Glycol)-Poly(Epsilon-Caprolactone) Microspheres." Journal of Material Science: Materials in Medicine, vol. 19, pp. 1033-1041, Aug. 15, 2017.
Mohapatra, J. et al., "Enhancement of Magnetic Heating Efficiency in Size Controlled MFe2O4 (M = Mn, Fe, Co and Ni) Nanoassemblies." The Royal Society of Chemistry, vol. 5, pp. 14311-14321, Jan. 21, 2015.
Mihaela, O., "Study About the Possibility to Control the Superparamagnetism-Superferromagnetism Transition in Magnetic Nanoparticle Systems." Journal of Magnetism and Magnetic Materials, vol. 343, pp. 189-193, May 15, 2013.
Oster, J. et al., "Polyvinyl-Alcohol-Based Magnetic Beads for Rapid and Efficient Separation of Specific or Unspecific Nucleic Acid Sequences." Journal of Magnetism and Magnetic Materials, vol. 225, pp. 145-150, Apr. 12, 2001.
Prodelalova, J. et al., "Isolation of Genomic DNA Using Magnetic Cobalt Ferrite and Silica Particles." Journal of Chromatography A, vol. 1056, Issues 1-2, pp. 43-48, Nov. 4, 2004.
Qiu, X. et al., "Preparation and Characterization of PVA Coated Magnetic Nanoparticles." Chinese Journal of Polymer Science, vol. 18, No. 6, pp. 535-539, 2000.
McBain, S. et al., "Polyethyleneimine Functionalized Iron Oxide Nanoparticles as Agents for DNA Delivery and Transfection." Journal of Materials Chemistry, vol. 17, pp. 2561-2565, Apr. 13, 2007.
Schweiger, C. et al., "Novel Magnetic Iron Oxide Nanoparticles Coated With Poly(Ethylene Imine)-G-Poly(Ethylene Glycol) for Potential Biomedical Application: Synthesis, Stability, Cytotoxicity and MR Imaging." International Journal of Pharmaceutics, vol. 408, Issues 1-2, pp. 130-137, Feb. 18, 2011.
Skowronski, E. et al., "Magnetic, Microplate-Format Plasmid Isolation Protocol for High-Yield, Sequencing-Grade DNA." Biotechniques, vol. 29, No. 4, pp. 786-792, Oct. 2000.

(56) References Cited

OTHER PUBLICATIONS

Taqaddas, A., "Use of Magnetic Nanoparticles in Cancer Detection With MRI." International Journal of Medical, Health, Biomedical, Bioengineering and Pharmaceutical Engineering, vol. 8, No. 9, 2014.

Tiraferri, A. et al., "Direct Quantification of Negatively Charged Functional Groups on Membrane Surfaces." Journal of Membrane Science, vol. 389, pp. 499-508, Nov. 20, 2011.

Ugelstad J. et al., "Preparation and Application of New Monosized Polymer Particles." Progress in Polymer Science, vol. 17, Issue 1, pp. 87-161, 1992.

Wang, L. et al., "Bacterial Inactivation Using Silver-Coated Magnetic Nanoparticles as Functional Antimicrobial Agents." Analytical Chemistry, vol. 83, No. 22, pp. 8688-8695, Oct. 14, 2011.

Wang, L. et al., "Monodispersed Core-Shell Fe3O4@Au Nanoparticles." Journal of Physical Chemistry B, vol. 109, No. 46, pp. 21593-21601, Oct. 27, 2005.

Wang, X. et al., "Synthesis, Characterization and Potential Application of MnZn Ferrite and MnZn Ferrite@Au Nanoparticles." Journal of Nanoscience and Nanotechnology, vol. 9, No. 5, pp. 3005-3012, May 2009.

Xu, J. et al., "Simultaneous, Single Particle, Magnetization and Size Measurements of Micron Sized, Magnetic Particles." Journal of Magnetism and Magnetic Materials, vol. 324, No. 24, pp. 4189-4199, Jul. 28, 2012.

English Translation of First Office Action; CN201580070417.8; dated Sep. 4, 2018, China Patent Office, 11 Pgs.

POLYMER-ENCAPSULATED MAGNETIC NANOPARTICLES

This is a national stage application under 35 U.S.C. § 371 of International Application No. PCT/US2015/057036, filed on Oct. 23, 2015, which claims the benefit of priority under 35 U.S.C. § 119 of U.S. Provisional Application Ser. No. 62/067,634 filed on Oct. 23, 2014 the content of which is relied upon and incorporated herein by reference in its entirety.

FIELD

The present disclosure relates generally to methods of making magnetic nanoparticles, and more specifically to polymer-encapsulated magnetic nanoparticles for, by way of example, the isolation of proteins, cells, and viruses and also for diagnostic applications and cell cultivation.

TECHNICAL BACKGROUND

Magnetic particles or beads are used within the biotechnology field in a range of applications including extraction and purification of nucleic acids and proteins as well as viruses and whole cells. During use, target media (e.g., DNA) binds to the surface of the particles, whereupon it can be manipulated magnetically.

It would be advantageous to provide a low-cost, efficient approach to synthesize and provide magnetic particles having, for example, a strong response to a magnetic field, controlled particle size, composition, uniformity, crystalline structure, and surface chemistry.

BRIEF SUMMARY

In embodiments, the present disclosure provides magnetic particles having a particle size of 500 nm or less, a magnetic core and a polymer coating that surrounds and encapsulates the core. The core includes a metal, metal alloy, or metal oxide of at least one metal such as B, Mg, Al, Mn, Co, Ni, Cu, Fe, Sm, La, Yb, Dy, Gd or Er and Nb. The magnetic core is polycrystalline particles which are superspin glass magnetic materials having coercivity greater than zero and magnetic remanence greater than zero at room temperature. An in situ hydrolysis/precipitation method from precursor metal salts is used to form the polymer-encapsulated magnetic particles without any polymerization reaction.

A method for making a magnetic particle comprises forming a solution including a metal precursor, an oxidizing agent or reducing agent, a polymer source, and a basic compound; and increasing the solution temperature to at least 50° C. to form magnetic particles having a core and a polymer coating that surrounds and encapsulates the core.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals and in which:

FIG. 10 shows the same data as FIG. 9, but blown up so that the detail can be seen.

DETAILED DESCRIPTION

Figure 1:
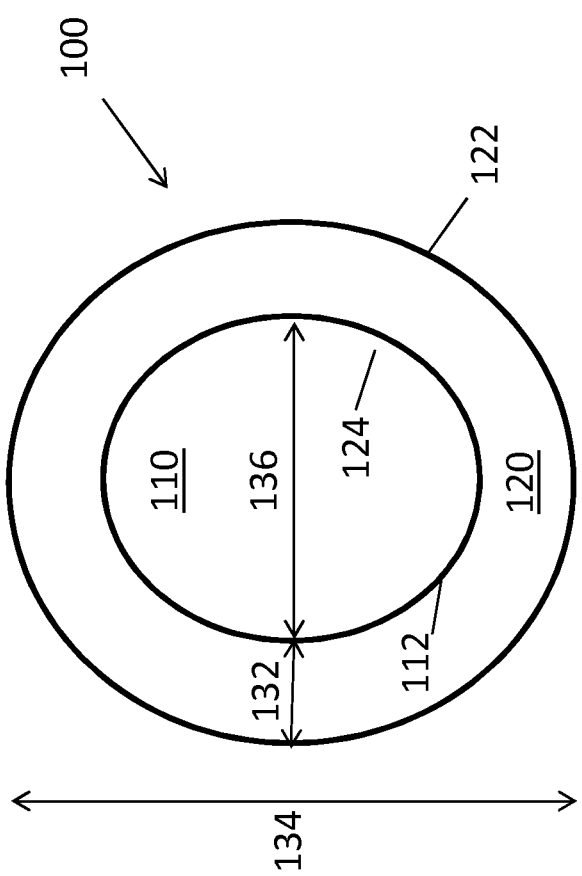
FIG. 1 is a schematic diagram of a magnetic particle according to one embodiment.

Reference will now be made in greater detail to various embodiments of the subject matter of the present disclosure, some embodiments of which are illustrated in the accompanying drawings. The same reference numerals will be used throughout the drawings to refer to the same or similar parts.

A single, magnetic particle 100 is shown schematically in cross-section in FIG. 1. Particle 100 includes a magnetic core 110 and a coating 120 that completely surrounds and encapsulates the core. The core 110 has an outer surface 112. The coating 120 is in direct physical contact with the outer surface 112 of the core 110 along an inner surface 124 of the coating 120. The magnetic particle 100 is also referred to as a magnetic nanoparticle (MNP). The polymer coating surrounds the magnetic core.

Figure 2:
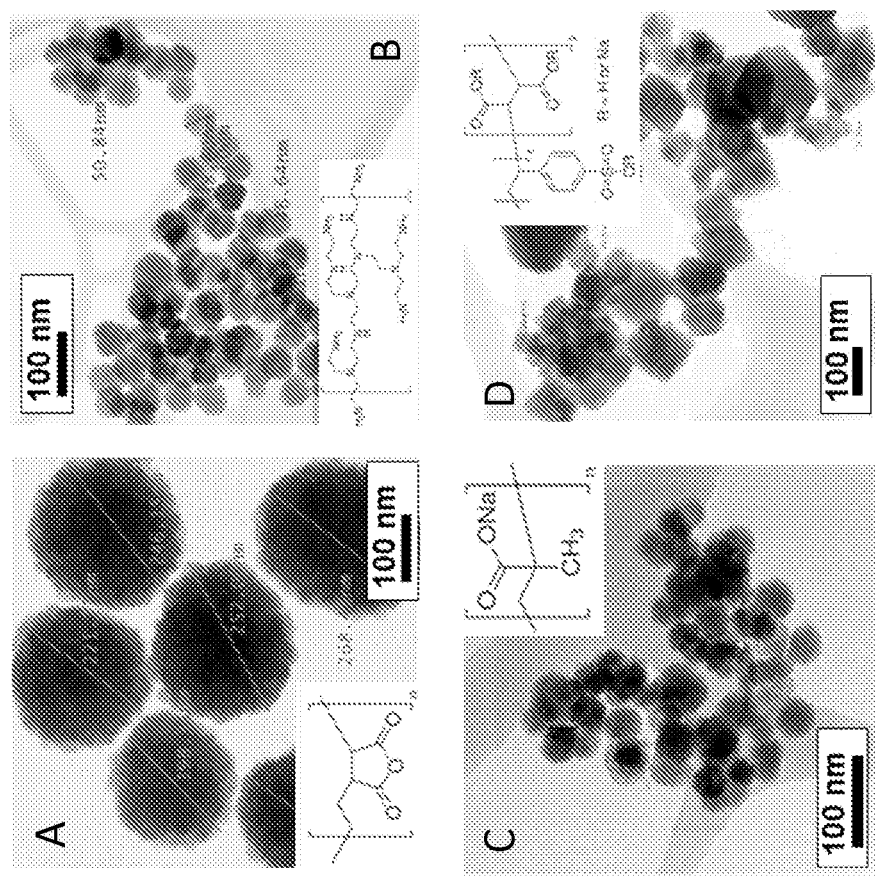
FIG. 2 shows TEM micrographs of magnetic particles using different surface-functionalized polymer.

The core comprises a polycrystalline, inorganic magnetic material. The polycrystalline or poly-nanocrystalline character of the core can be seen in FIGS. 2 A, B, C and D. FIG. 2 shows TEM micrographs of surface-functionalized magnetic particles, and includes several embodiments (A) PEMA-$Fe_3O_4$, (B) PEI-$Fe_3O_4$, (C) PMAA-$Fe_3O_4$, and (D) PSSMA-$Fe_3O_4$. As can be seen in FIG. 2, in embodiments, the magnetic particles show a crystalline structure. As is especially evident in FIG. 2A, the magnetic core appears to be clumps or spheres made from individual small particles or crystals. In addition, the crystals are uniform. That is, the crystals are all the same crystalline phase (see, for example, FIG. 7) The crystals are coalesced (>2 single crystals directly contact each other) to form a core or clump of crystals contained within the polymer shell.

Figure 3:
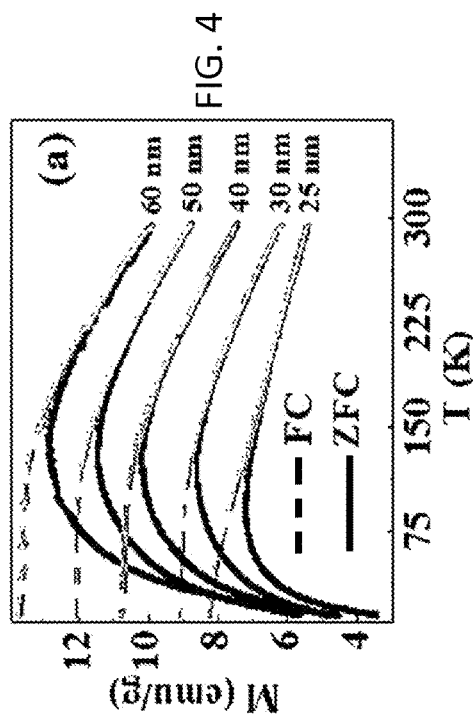
FIG. 3 is a graph illustrating the magnetic field ($\chi$) versus temperature (K) of different magnetic properties. (from http://electrons.wikidot.com/magnetism-iron-oxide-magnetite).

Magnetism is the term for describing magnetic properties and magnetic phenomena. There are six types of magnetism in traditional bulk materials: Diamagnetism, paramagnetism, ferromagnetism, ferromagnetism, antiferromagnetism, and spin glass-type behavior. In all fine-particle systems, including nanoparticles, different kinds of magnetic interparticle interactions exist and the interaction strength varies with their volume concentration. These properties are illustrated, in part, in FIGS. 3-6. Magnetic materials such as, for example, $Fe_3O_4$, can exhibit magnetic characteristics that are temperature dependent. FIG. 3 is a graph illustrating the magnetic field ($\chi$) versus temperature (K) of different magnetic properties. (from http://electrons.wikidot.com/magnetism-iron-oxide-magnetite). Line 310 plots the magnetic characteristic of ferromagnetic material. Line 312 plots the magnetic characteristic of paramagnetic material and line 314 plots the magnetic characteristic of antiferromagnetic material. Ferromagnetic material (310) and paramagnetic material (312) show decreasing magnetic susceptibility ($\chi$) with increasing temperature. Antiferromagnetic material also shows decreasing magnetic susceptibility with increasing temperature above room temperature.

Without being limited by theory, this may be because increasing temperature disrupts the alignment of electrons within the ferrous material. With increasing temperature, electrons become more randomly oriented, which causes the magnetic moment to decrease, as is seen in FIG. 3. As temperature decreases, at the Curie point (shown at 311), ferromagnetic material "freezes" and the material becomes significantly more magnetic as the electrons align within the material. Similarly, in paramagnetic material, magnetism decreases with increasing temperature as shown in line 312.

And, antiferromagnetic material shows a peak magnetism at the Néel point, shown at 313, before the magnetism of the material decreases with increasing temperature. The Néel point is the temperature above which an antiferromagnetic material becomes paramagnetic, that is, the thermal energy becomes large enough to destroy the macroscopic magnetic ordering within the material. The Néel point is analogous to the Curie temperature for ferromagnetic materials (from https://en.wikipedia.org/wiki/N%C3%A9el_temperature).

Figure 4:
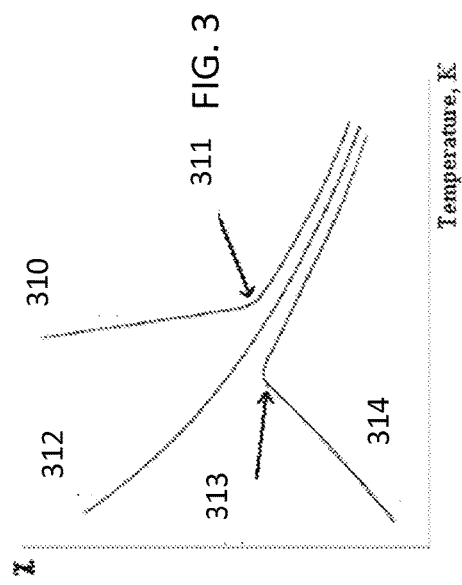
FIG. 4 is a plot of Magnetic Moment vs temperature for superparamagnetic $Fe_3O_4$. (from J. Mohapatra, et. al., RSC Adv., 2015, 5, 14311)

Superparamagnetism occurs when the particle size of a magnetic material reaches a critical size. The critical size depends on the material. For example the critical size for $Fe_3O_4$ is about 29~36+/−0.5 nm. The critical size for $\gamma$-$Fe_2O_3$ is 30 nm. When a magnetic material reaches a critically small size, each particle can be treated as a single "domain" or a single electron. In these single-domain ferro- or ferromagnetic (FM) nanoparticles the magnetization is considered to align with parallel or antiparallel to easy axis, which is an energetically favorable direction of spontaneous magnetization. For a small enough single-domain particles the energy barrier becomes so small that energy fluctuation can overcome the anisotropy energy and spontaneously reverse the magnetization of a particle from one easy direction to the other, even in the absence of an applied field. Thus, such FM nanoparticles can be treated as single magnetic units, which are freely and randomly fluctuating like paramagnetism, so it is called superparamagnetism. For example, FIG. 4 illustrates a graph plotting magnetic moment vs temperature for superparamagnetic $Fe_3O_4$ material (taken from J. Mohapatra, et. al. RSC Adv., 2015, 5. 14311). Again, as temperature increases, in the absence of a magnetic field (ZFC), magnetism decreases. When temperature is reduced in the presence of a magnetic field (FC), magnetism increases.

Magnetic susceptibility is represented by the symbol $\chi$ which is a dimensionless quantity. M is the magnetic moment and its unit is emu/g. The relationship between magnetic susceptibility ($\chi$) and magnetic moment (M) is represented by Formula 1, where $\chi$ is magnetic susceptibility, M is magnetic moment and H is the applied field:

$$\chi = \frac{M}{H} \qquad \text{Formula 1}$$

So, as shown in FIG. 3 and FIG. 4, $\chi$ and M have same trend but different unit and value. Table 1 shows typical behavior of different types of magnetic material with changes in temperature. For example, M is the a mass magnetization ($M_g$) in emu/g=$A \cdot m^2$/kg; and H=1 oe=$1 \times 10^3$/($4\pi$) A/m. From Formula 1, the magnetic susceptibility of the materials can be derived $\chi = M_g 4\pi \times 10^{-3} \rho$. $\rho$ is the density of materials ($m^3$/kg).

TABLE 1

Magnetic susceptibilities temperature dependence for different types of magnetism) (from Anthony R. West, Basic Solid State Chemistry, 2nd ed. John Wiley & Sons Ltd. (England), 1999, p375)

| Behaviour | Typical $\chi$ value | Change of $\chi$ with increasing temperature | Field dependence? |
|---|---|---|---|
| Diamagnetism | $-8 \times 10^{-6}$ for Cu | None | No |
| Paramagnetism | | Decreases | No |

TABLE 1-continued

Magnetic susceptibilities temperature dependence
for different types of magnetism) (from Anthony
R. West, Basic Solid State Chemistry, 2nd ed. John
Wiley & Sons Ltd. (England), 1999, p375)

| Behaviour | Typical χ value | Change of χ with increasing temperature | Field dependence? |
|---|---|---|---|
| Pauli paramagnetism | 8.3 × 10⁻⁴ for Mn | None | No |
| Ferromagnetism | 5 × 10³ for Fe | Decreses | Yes |
| Antiferromagnetism | 0 to 10⁻² | Increases | (Yes) |

Figure 6:
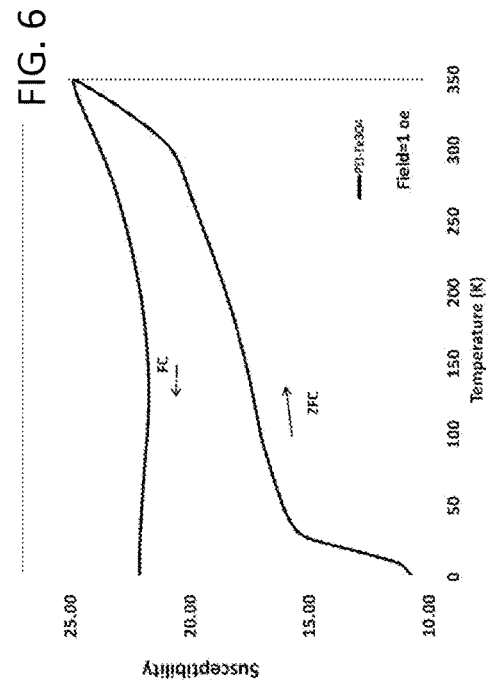
FIG. 5 and FIG. 6 are plots showing susceptibility ($\chi$) vs temperature for two embodiments of MNPs.
Figure 5:
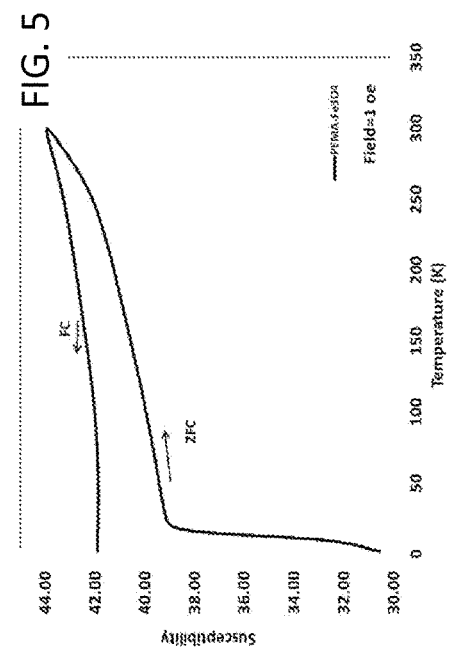

FIG. 5 and FIG. 6 are plots showing magnetic susceptibility ($\chi$) vs temperature for two embodiments of MNPs. FIG. 5 is a measurement taken from PEMA-Fe$_3$O$_4$ and FIG. 6 is a measurement taken from PEI-Fe$_3$O$_4$. As can be seen in FIG. 5 and FIG. 6, in embodiments, MNPs show temperature dependent behavior that cannot be described as paramagnetic, ferromagnetic, antiferromagnetic or superparamagnetic alone. The MNPs, in embodiments, continue to increase in magnetic moment with increasing temperature like antiferromagnetism, through room temperature (which in Kelvin is at approximately 300 degrees). However, the values of magnetic susceptibility are 10~22 and 30~42 for PEMA-Fe$_3$O$_4$ and PEI-Fe$_3$O$_4$, respectively, which are three magnitude higher than conventional antiferromagnetism in Table 1. That is, the magnetic moment of the magnetic particles increases as the temperature increases above room temperature. The magnetic susceptibility trends of two embodiments of MNPs at low temperature (2-350K) cannot be fitted into conventional magnetism, as well most of superparamagnetic magnetite. There is no indication that a maximum had been reached in the experimental temperature range, which indicates the blocking temperatures (TB) for all samples are well above room temperature 300 K.

This behavior is relevant for practical applications of MNPs, in embodiments. For example, experiments including extraction and purification of nucleic acids and proteins as well as viruses and whole cells benefit from particles having enhanced magnetic moment. During use, target media (e.g., DNA) binds to the surface of the particles, where it can be manipulated magnetically. These uses are generally performed at room temperature or higher, such as DNA melting temperature. In embodiments, MNPs exhibit increased magnetic moment or magnetic susceptibility at room temperature and up to 350K (77° C.), compared to other magnetic materials.

The small individual unite crystals of the magnetic core of MNPs, in embodiments, are less than 15 nm in diameter or less than 30 nm in diameter or less than 50 nm in diameter. The individual magnetic crystals are superparamagnetic. Usually, superparamagnetic particles, if sufficiently dispersed in a solution or in a matrix, exhibit zero remanence (the residual magnetism remaining in the material after a magnetic field has been removed) and zero coercivity (the reverse field needed to reduce the magnetization to zero after saturation). In addition, due in part to the methods used to manufacture MNPs in embodiments, the particles, embedded or captured in a polymer shell, cluster together. Because the poly-nanocrystalline material clusters together or coalesces, there is some level of interaction between the individual unite crystals. Magnetic force (Fm) is described in Formula 2 and Formula 3 where m is magnetic moment of the particle, B is an applied magnetic field, Vm is the volume of the particle, $\Delta\chi$ is the difference in magnetic susceptibilities between the particle and the surrounding medium, $\nabla$ is the gradient, the change of the magnitude of the vectors m and B per unit distance, and $\mu_0$ is a constant $4\pi \times 10^{-7}$ (T m A$^{-1}$).

$$Fm = (m \cdot \nabla)B \qquad \text{Formula 2}$$

$$Fm = Vm\Delta\chi\nabla\left(\frac{B^2}{2\mu_0}\right) \qquad \text{Formula 3}$$

This collective behavior or interaction creates a degree of remanence and coercivity in the particles. The nanocrystals or polycrystals within the magnetic core of these MNPs are in close contact. They are clumped together or coalesced, within a polymer coating. Because they are so close together, there is strong exchange coupling and magnetic ordering between the interfaces of the nanocrystals in the magnetic core. This leads to a decrease in the anisotropic energy, which allows increases in the total magnetic moment for these particles, according to Formula 4.

$$m_{total} \sum_{\substack{i,j \\ i \neq j}} m_i + m_j + \Delta m_i m_j \qquad \text{Formula 4}$$

According to the literature (J. Mohapatra, et. al. RSC Adv., 2015, 5. 14311), the saturation magnetization (Ms) for assembled nanoparticles are found to be higher as compared to that of the reported single nanocrystals counterparts. Meanwhile, the Ms values for spinel structured oxide, such as [Fe$^{3+}$]$^{tet}$[M$^{2+}$, Fe$^{3+}$]$^{oct}$O$_4$, strongly depend on the magnitude of the M$^{2+}$ cation magnetic moment, because Fe$^{3+}$ ions on tetrahedral and octahedral sites with opposed spins, causes the net moment of the Fe$^{3+}$ ions to be zero. Therefore, the control of doped M$^{2+}$ and magnetic coupling can used to design a high Ms materials for applications requiring high Ms materials.

In all fine-particle systems, including nanoparticles, different kinds of magnetic inter-particle interactions exist and the interaction strength varies with their volume concentration. Usually in the case of low concentrations of particles and sufficiently high temperatures, only superparamagnetism (SPM) behavior is observed because of negligible interparticle interactions. However, when particle concentration increase and inter-particle distances decrease, inter-particle interactions are non-negligible, and a collective behavior is observed. At sufficiently strong interactions a magnetic nanoparticle ensemble can show superspin glass (SSG) properties similar to those of atomic spin glass systems in bulk. With a further increase in concentration, but still below physical percolation, sufficiently strong interactions can be experienced to form a superferromagnetic (SFM) state.

Figure 7:
FIG. 7 shows X-ray powder diffraction measurements of three MNPs, in embodiments. Plot a is PEMA-$Fe_3O_4$ from Example 1, b is PEMA-$Fe_3O_4$ from Example 1, and c is PEI-$Fe_3O_4$ from Example 2.

FIG. 7 shows X-ray powder diffraction measurements of three MNPs, in embodiments. Plot a is PEMA-Fe$_3$O$_4$ from Example 1, b is PEMA-Fe$_3$O$_4$ from Example 1, and c is PEI-Fe$_3$O$_4$ from Example 2. FIG. 7 shows the composition and crystalline structure of the magnetic particles, and indicates that all MNPs are pure Fe$_3$O$_4$ with inverse cubic spinel crystalline structure. The morphology of FIG. 2D appears to be very different from the crystalline structure of FIG. 2A, but XRD (FIG. 7) shows they have same pure Fe$_3$O$_4$ crystalline structures with slight difference in peak width that corresponds to single crystal size.

Figure 8:
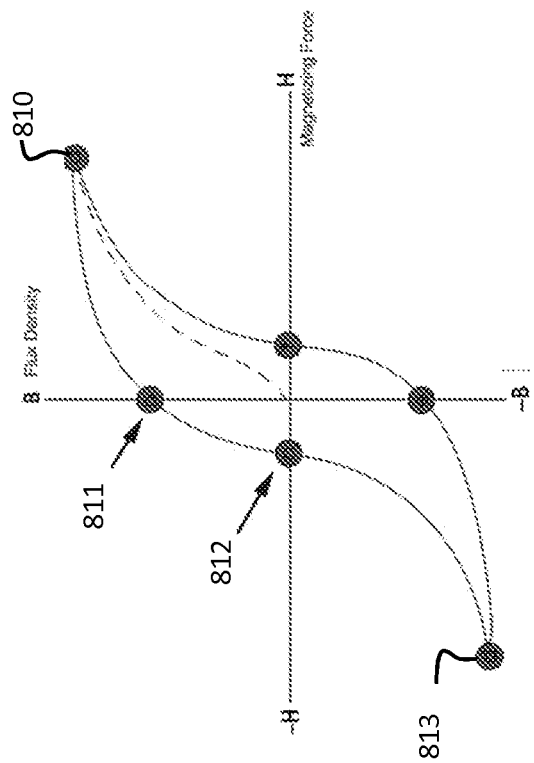
FIG. 8 is a hysteresis loop illustrating properties of magnetic materials.

FIG. 8 is a hysteresis loop illustrating properties of magnetic materials, plotting magnetizing force H on the X axis against flux density (on the Y axis). Properties of magnetic materials can be measured from a hysteresis loop. 810 is saturation, 811 is retentivity, 812 is coercivity and 813 is saturation in the opposite direction.

Figure 10:
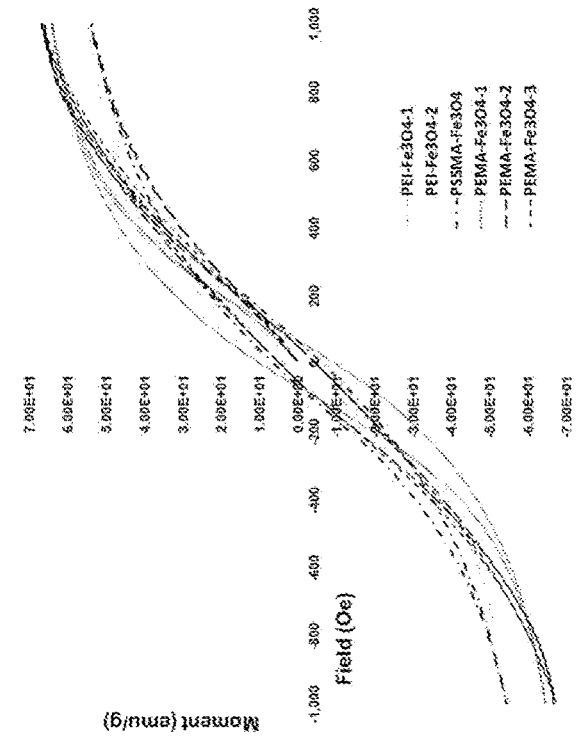
FIGS. 9 and 10 are measured hysteresis loops plotting magnetic moment (emu/g) vs magnetic field (Oe) in embodiments of MNPs.
Figure 9:
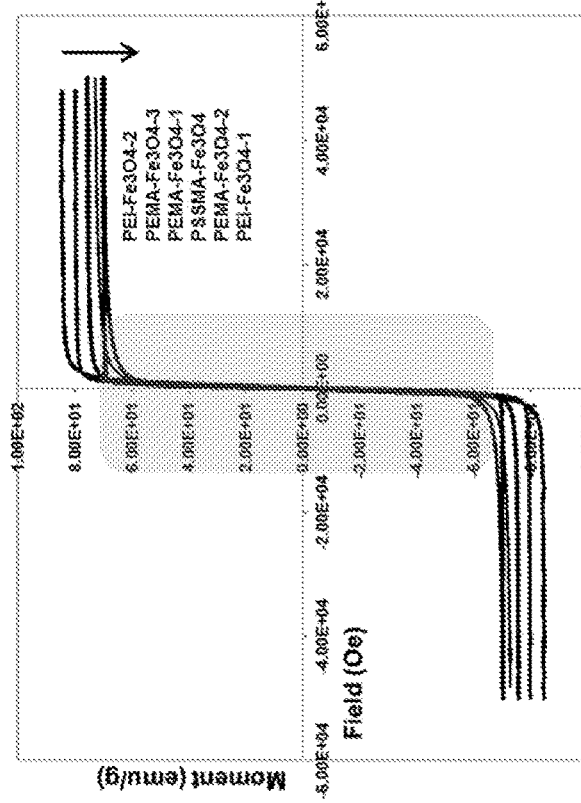

FIG. 9 and FIG. 10 are graphs plotting magnetic moment (emu/g) vs magnetic field (Oe) in embodiments of MNPs, in a hysteresis loop, as was shown in FIG. 8. FIG. 10 shows the same data as FIG. 9, but blown up so that the detail can be seen. Coercivity measurements were taken from the plot of FIG. 10 and are presented below in Table 2. All measurements shown in Table 2 were taken at room temperature.

TABLE 2

| | Sample | | | | | |
|---|---|---|---|---|---|---|
| | PEI-Fe3O4-1 | PEI-Fe3O4-2 | PSSMA-Fe3O4 | PSSMA-Fe3O4-1 | PEMA-Fe3O4-2 | PEMA-Fe3O4-3 |
| Magnetic core size (nm) | 30-50 | 140-200 | 18-30 | 180-220 | 160-260 | 140-230 |
| Saturation magnetization (emu/g) | 70.32 | 84.97 | 72.90 | 75.75 | 70.19 | 79.97 |
| Coercivity $H_c$ (oe) | 30 | 150 | 70 | 70 | 50 | 50 |
| Magnetic moment remanence (emu/g) | 3 | 8 | 6 | 10 | 5 | 5 |

In embodiments, MNPs have remanence and coercivity, as shown in Table 2. Because the magnetic particles, in embodiments, exhibit superparamagnetism (the crystals, or nanocrystals, that are grouped together to form a magnetic core, are small and are of a critical size so that each particle can be considered a single domain). Single domains within the magnetic core may range in size from 0.5 nm to 200 nm, e.g., 0.5, 1, 2, 5, 10, 50, 100 or 200 nm, including ranges between any of the foregoing. These small single crystal domains are superparamagnetic.

These interparticle magnetic interactions result in measurable remanence and coercitivity (as shown in Table 2). This remanence and coercivity can be considered collective behavior. This combination of superparamagnetism and collective behavior is what is known as "superspin glass" magnetic behavior. Superspin glass particles show high magnetic moment and provide a stronger magnetic response compared with superparamagnetic particles alone. In embodiments, the MNPs provided herein comprise superspin glass, polycrystalline or polynanocrystalline, magnetic particles which have coercivity greater than 0 oe, or coercivity from 0 to 300 oe, or coercivity in any range between 0 and 300 or, for example, in the range of 30 to 150 oe. By way of example, the coercivity of the particles may be 10, 20, 50, 100, 150, 200, 250 or 300 Oe, including ranges between any of the foregoing. In embodiments, MNPs provided herein comprise poly crystalline particles which are superparamagnetic and which are coalesced to form superspin glass magnetic core. These superspin glass polycrystalline or polynanocrystalline magnetic particles have a magnetic moment remanence (emu/g) greater than zero, or in the range from zero to 12 or in any range between zero and 12, for example in the range of from 3 to 10 (emu/g). In addition, in embodiments the MNPs exhibit high saturation magnetization (emu/g). For example, in embodiments, the MNPs exhibit saturation or saturation magnetization than 70 emu/g at room temperature. Higher magnetization can provide fast magnetic response. And, possessing high magnetization at room temperature allows these materials to possess faster magnetic response at room temperature.

As a result of the superspin glass properties of the magnetic core, the magnetic particles exhibit low but not zero coercivity (e.g., less than 300 Oe) and high magnetization (e.g., at least 50 emu/g). Soft magnetic materials are characterized by very low (or zero) coercivity and high saturation magnetization. (Osaci Mihaela, "Study about the possibility to control the superparamagnetism-superferromagnetism transition in magnetic nanoparticle system", Journal of magnetism and magnetic materials, 2013, 343, 189-193). Soft magnetic materials are those materials that are easily magnetised and demagnetised. They typically have intrinsic coercivity great than 10,000 Am-1 is considered "hard". (Introduction to Magnetism and Magnetic Materials, 2nd Edition, By David C. Jiles). These characteristics make these MNPs soft magnetic particles. Soft magnetic materials are materials that are easy to magnetize and demagnetize. Soft magnetic materials magnetize to saturation and experience a reversal in polarity in relatively weak magnetic fields at 25° C. In use, the high magnetization of the particles promotes a rapid magnetic response and high magnetic separation efficiency. The high binding capacity of the particles enables a more efficient and economic materials utilization, whereby a greater number of samples can be processed within a given container volume per assay. In embodiments, the core material exhibits superparamagnetism and superspin glass magnetism.

In embodiments, the MNPs are different from other commercially available materials which contain nano sized superparamagnetic materials, such as M-280 and M-450 beads (Dynabeads®), available through ThermoFisher Scientific, Waltham, Mass. According to a published study (Xu, et al., *Simultaneous, single particle, magnetization and size measurements of micron sized, magnetic particles* J Magn Magn Materi. 2012 Dec. 1; 324(24): 4189-4199, available at http://www.ncbi.nlm.nih.gov/pmc/articles/PMC3433070/) these beads exhibit zero coercivity, zero remanence and saturation magnetization values are 10 emu/g and 19 emu/g for the M=280 and M-450 beads respectively. At room temperature (T=300K), in embodiments, MNPs exhibit higher saturation magnetization (50<Ms<100 emu/g,), non-zero coercivity and non-zero remanence while commercial products exhibit zero coercivity and zero remanence. Without being limited by theory, this lack of remanence and coercivity may be because other magnetic particles are separated by the matrix that they are imbedded in, in the case of low concentrations of particles and sufficiently high temperatures, only superparamagnetism behaviour is observed because of negligible interparticle interactions, which does not allow for superspin glass magnetic characteristics.

The core material may comprise a metal, metal alloy, or metal oxide, as well as combinations thereof. An example core material is iron oxide ($Fe_3O_4$), though the core may comprise a metal, metal alloy or metal oxide comprising one or more transition metals (B, Mg, Al, Mn, Co, Ni, Cu and Fe) and/or one or more lathanides i.e. Sm, La, Yb, Dy, Gd, Er, and Nb. In one example, the magnetic core comprises iron oxide doped with boron or aluminum. Further example core materials include cobalt oxides, nickel oxides, spinel compositions such as $CuFe_2O_4$, $NiFe_2O_4$, $MnFe_2O_4$, or $MgFe_2O_4$ and intermetallic compositions such as NiFe or NiCoFe. In embodiments, the magnetic core comprises at least 60 wt. % of the particle.

In addition to a magnetic core, MNPs comprise a polymer material or a mixture of polymer materials. The polymer molecules may or may not be cross-linked. Suitable polymers include polyacids, poly alcohols, and polyamines.

Example polymer materials include poly(ethyl methacrylate) or poly(ethylene-alt-maleic anhydride) (PEMA), poly (methyl methacrylate) (PMMA), polyetheramine (PEI), poly (methacrylic acid) (PMAA), poly(4-styrene sulfonic acid-co-maleic acid) (PSSMA), polyacrylic acid, polyvinyl alcohol, poly thiol, poly mercapto acid, as well as mixtures and co-polymers thereof. In embodiments, sodium salt solutions of the poly(methacrylic acid) or the poly(4-styrene sulfonic acid-co-maleic acid) may be used.

As illustrated in FIG. 1, the core 110 has a magnetic core size 136, and the magnetic bead or MNP 100 has a particle size 134. In embodiments, the size of the core ranges from about 10 to 250 nm, e.g., 10, 20, 30, 40, 50, 100, 200 or 250 nm, including ranges between any two of the foregoing. Actual measured magnetic core sizes, in embodiments, are reported in Table 2 and range from 18-230 nm in diameter, although other magnetic core sizes are contemplated.

The term "particle size" or "bead size" is used to describe the maximum linear dimension associated with a magnetic bead, or a MNP. In the case of a spherical particle, for example, the particle size is the diameter. In the case of an oblong particle, the particle size is the "length" of the particle. An example average particle size for a plurality of magnetic particles 100 may range from about 20 nm to 500 nm, e.g., 20, 30, 40, 50, 100, 200, 300, 400 or 500 nm, and may be defined for a given material batch over a range of any two of the aforementioned values. By providing magnetic nanoparticles within the disclosed range of particle sizes, the suspension of particles is sufficient to provide acceptable binding capacity without undesired settling of the particles, which is a drawback of larger (greater than 500 nm) particles.

The coating 120 has a thickness 132 defined as the average shortest distance between the inner surface 124 of the coating and the outer surface 122 of the coating. In embodiments, the coating may have a substantially uniform thickness or a variable thickness depending, for example, on the method used to form the coating. An example average thickness for the coating 124 may range from about 10 nm to 250 nm, e.g., 10, 20, 30, 40, 50, 100, 200 or 250 nm, including ranges between any two of the foregoing.

In some embodiments, the magnetic particle 100 may be substantially spherically shaped. However, other shapes are contemplated herein, such as, but not limited to asymmetric shapes or spheroids. In embodiments, the disclosed magnetic nanoparticles have a particle density of at least 3 g/cm³, e.g., 3, 3.5 or 4 g/cm³. In further embodiments, the disclosed magnetic nanoparticles have a particle density greater than 4 g/cm³. In embodiments, the magnetic nanoparticles have a surface area of at least 10 m²/g, e.g., 10-20 m²/g.

Methods of making the magnetic particles, in embodiments, involve combining, in solution, a soluble metal precursor, an oxidizing agent or reducing agent, a polymer source, and a basic compound. The methods are performed in the absence of a polymerization reaction to form the polymer shell. The solution may be an aqueous or non-aqueous solution. In embodiments, the synthesis is performed in an inert atmosphere (i.e., oxygen-free atmosphere). Example non-aqueous solvents include polyethylene glycol (PEG), dimethylformamide (DMF), tetrahydrofuran (THF), and other polar or non-polar solvents, as well as mixtures thereof. Example solution compositions are summarized in Table 3.

TABLE 3

Example solution compositions for MNP synthesis

| Component | Solution composition (wt. %) |
| --- | --- |
| Metal precursor | >0-40 |
| Oxidizing agent or Reducing agent | >0-50 |
| Polymer | >0-30 |
| Basic compound | >0-10 |

The solution for the MNP synthesis can comprise up to 40 wt. % metal precursor, e.g., 2, 5, 10, 20, 30 or 40 wt. %, including ranges between any of the foregoing, up to 50 wt. % oxidizing agent or reducing agent, e.g., 2, 5, 10, 20, 30, 40 or 50 wt. %, including ranges between any of the foregoing, up to 30 wt. % polymer, e.g., 2, 5, 10, 20 or 30 wt. %, including ranges between any of the foregoing, and up to 10 wt. % basic compound, e.g., 1, 2, 5 or 10 wt. %, including ranges between any of the foregoing.

Example metal precursors include metal salts such as metal sulfates, metal nitrates, metal chlorides, metal perchlorates, metal carbonates and metal acetylacetonates. In embodiments, the metal salts are $M^{2+}$ salts, i.e., in the case of iron salts, ferrous salts such as iron (II) sulfate ($FeSO_4$), iron (II) acetate ($Fe(C_2H_4O_2)_2$), iron (II) oxalate ($Fe(C_2O_4)$), iron (II) chloride ($FeCl_2$), iron (II) perchlorate ($Fe(ClO_4)_2$), iron (II) carbonate ($FeCO_3$), and iron (II) acetylacetonate ($[CH_3COCH=C(O)CH_3]_2Fe$). In embodiments, the metal precursor is an $M^{2+}$ salt and is free of higher oxidation state ions, i.e., free of $M^{3+}$ or $M^{4+}$ moieties.

The mixture of the metal precursor and the polymer source further comprises an oxidizing agent such as hydrogen peroxide ($H_2O_2$), sodium nitrate ($NaNO_3$), potassium nitrate ($KNO_3$), or trimethylamine oxide ($(CH_3)_3NO$) though other oxidizing agents may be used. In solution, the $M^{2+}$ precursors are partially oxidized to $M^{3+}$ by the oxidizing agent.

As an alternative to the oxidizing agent, a reducing agent may be used. In such embodiments, the mixture of the metal precursor and the polymer source further comprises a reducing agent such as hydrazine, an organic acid alkali salt (sodium citrate), alcohol, or ketone. In solution, the $M^{2+}$ precursors are partially reduced to $M^{1+}$ or completely reduced to $M^0$ by the reducing agent.

The addition to the solution of a basic compound such as sodium hydroxide (NaOH) increases the pH of the mixture, which hydrolyzes the metal to form a hydroxide, for example $Fe(OH)_x$, and together with an increase in the solution temperature to at least 50° C. (e.g., 50° C. to 100° C.) converts the hydroxide to an oxide ($Fe_3O_4$). Other example basic compounds include potassium hydroxide, ammonium hydroxide, and some organic bases, such as tetramethylammonium hydroxide, tetrabutylammonium hydroxide, or choline hydroxide are hydroxide donors. Once the hydroxide is de-hydrolyzed, the polymer attaches to the surface of the oxide particles.

Figure 11:
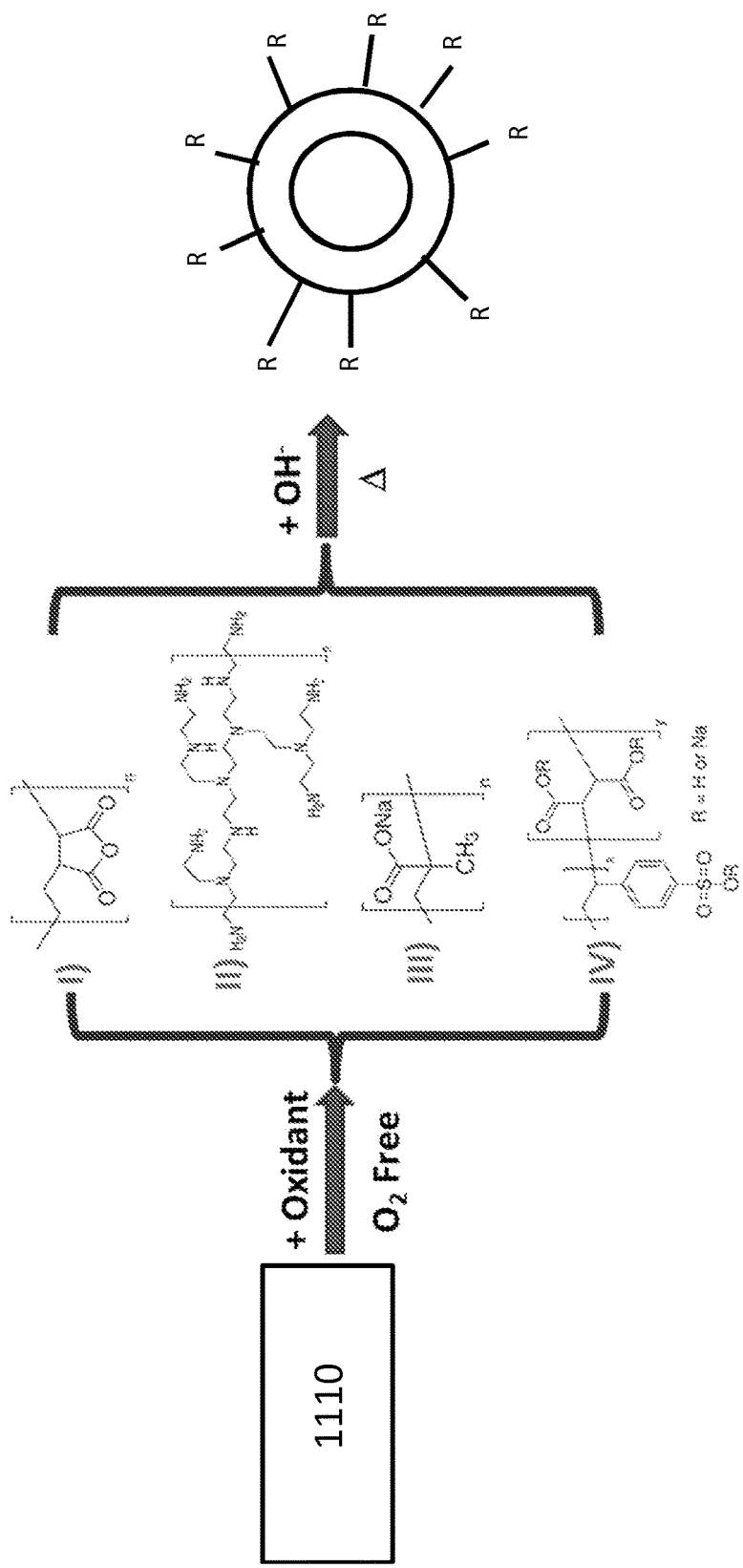
FIG. 11 is a flowchart illustrating synthesis of magnetic particles according to various embodiments.

A schematic depicting an MNP synthesis, in embodiments, is shown in FIG. 11. FIG. 11 illustrates the combination of a metal salt 1110 such as a ferrous salt or a $M^{2+}$ salt. This metal salt is combined, in the present of an oxidant and in an oxygen-free environment, with a suitable polymer. Four suitable polymers are illustrated in FIG. 11, and they include I) poly(ethylene-alt-maleic anhydride or PEMA; II) polylethlenimine or PEI; III) poly(methacrylic acid, sodium salt) solution or PMAA and IV) poly(4-styrenesulfonic acid-co-maleic acid) sodium salt or PSSMA, followed by the addition of a basic compound to form the MNP.

In embodiments, this in situ synthesis provides an appropriate level of particle aggregation, which enables the formation of discrete particles or discrete particles that group together to form magnetic cores (as shown in FIG. 2) which are clumped or grouped together sufficiently to experience collective behavior, and exhibit coercivity and remanence, while still having nanoscale dimensions. Notably, both the core and the coating are derived from solution without polymer polymerization, e.g., via hydrolysis and precipitation (e.g., crystallization).

In the resulting magnetic particles, the polymer coating may comprise from about 2 to 40 wt. % of the total mass of the particles. For instance, the coating may comprise 2, 5, 10, 15, 20, 25, 30, 35 or 40 wt. % of the total particle mass, including ranges between any of the foregoing. Thus, the core may comprise 60 to 98 wt. % of the total mass of the particles.

Figure 12:
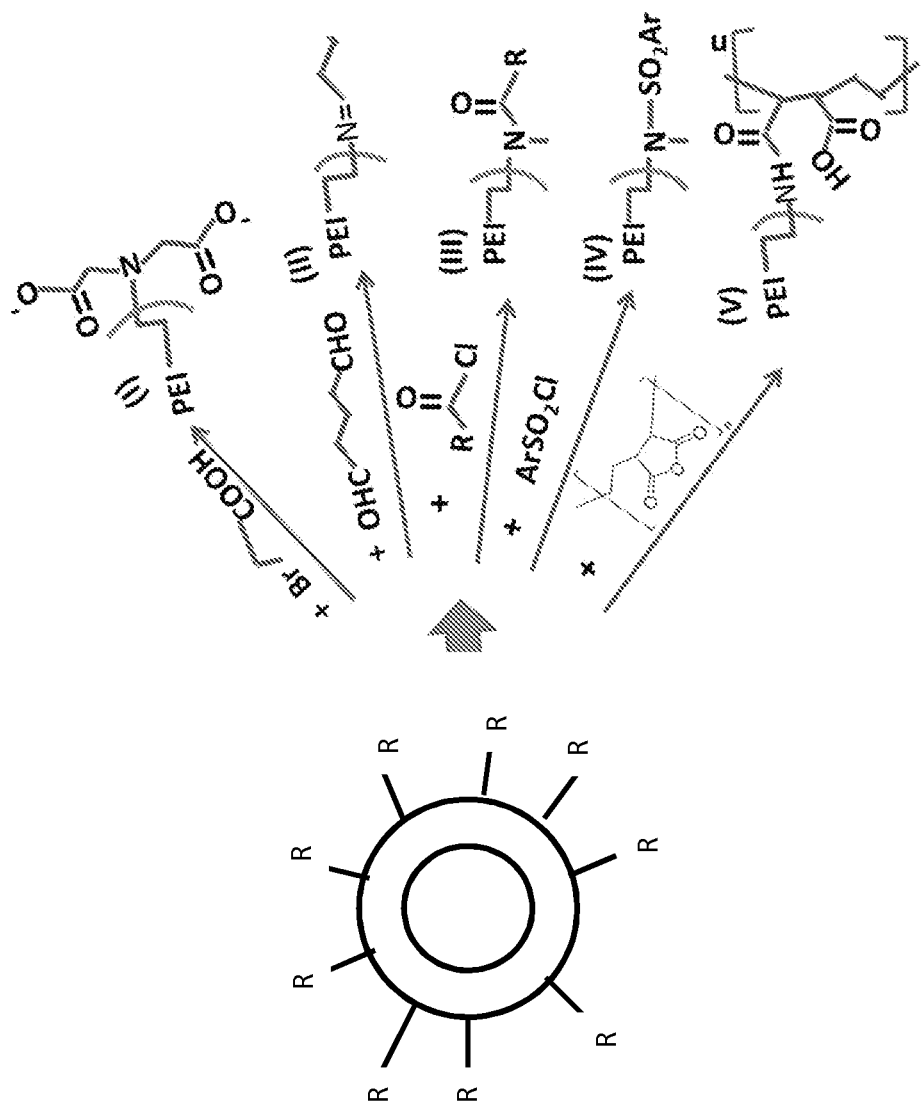
FIG. 12 is a schematic illustration of a surface-functionalized magnetic particle according to various embodiments.

In embodiments, one or more functional groups R can be incorporated onto the particle surface. Example functional groups include carboxylic acid/carboxylate groups, imine/amino groups, methyl groups, methylene groups, thiol groups, anhydride groups, phosphoric acid groups, sulfuric acid/sulfonate groups, sulfonamide or phosphatide groups. The R group in the embodiment shown in FIG. 12 can be, for example, an amino group.

The magnetic particle material can be used to bind biomolecules and separate the bound biomolecule by magnetic force. The bound molecules can then be reversibly released, i.e., through use of an appropriate buffer. Magnetic particles comprising a magnetic core, a PEI shell and various example functional groups are illustrated schematically in FIG. 12 Scanning transmission electron microscope (STEM) micrographs of MNPs having a PEI shell are shown in FIG. 2 B.

In embodiments, the disclosure provides magnetic particles having a magnetic core and a polymer coating; wherein the magnetic core comprises a metal, metal alloy, or metal oxide of at least one metal selected from the group consisting of B, Mg, Al, Mn, Co, Ni, Cu, Fe, Nb, Sm, La, Yb, Dy, Gd or Er; wherein the magnetic core comprises poly crystalline particles which are superparamagnetic and which are coalesced to form a superspin glass magnetic core; wherein the polymer coating surrounds the magnetic core; and wherein the magnetic particles exhibit coercivity greater than zero and less than 300 Oe, or the coercivity is between 30 and 150 Oe. Oe and magnetic remanence greater than zero and less than 12 emu/g at room temperature; and wherein the magnetic particle has a particle size of 500 nm or less. In embodiments, the poly crystalline particles of the magnetic core are the same crystalline phase and the magnetic moment of the magnetic particle increases as the temperature increases above room temperature. In embodiments, the magnetic particles polycrystalline particles which have coalesced to form a superspin glass magnetic core is a soft magnetic material. In embodiments, the coercivity is between 30 and 150 Oe, or the remanence is between 3 and 10 emu/g at room temperature. In embodiments, the polymer coating is selected from the group consisting of poly(ethyl methacrylate), poly(ethylene-alt-maleic anhydride), poly(m-ethyl methacrylate), polyethylene imine, poly(methacrylic acid), poly(4-styrene sulfonic acid-co-maleic acid), polyacrylic acid, polyvinyl alcohol, poly thiol, and poly mercapto acid or a combination. In embodiments, the core comprises at least 60 wt. % of the particle. In embodiments, the magnetic particles have a diameter of 10 to 250 nm. In embodiments, the polymer coating has an average thickness of between 10 nm to 250 nm. In embodiments, the magnetic particles have a surface functional group selected from the group consisting of carboxylate/carboxylic acid, amino/imine, methyl, methylene, thiol, anhydride, phosphoric acid, sulfonate/sulfuric acid, sulfonamide, and phosphatide. In embodiments, the magnetic core comprises $Fe_3O_4$.

In embodiments, the disclosure also provides a method of making a magnetic particle, comprising: forming a solution including a metal precursor, an oxidizing agent or reducing agent, a polymer source, and a basic compound; and increasing the solution temperature to at least 50° C. to form magnetic particles having a superspin glass core and a polymer coating that surrounds and encapsulates the core. In embodiments, the solution is aqueous. In embodiments, the mass ratio of metal to polymer in the solution ranges from 1:0.05 to 1:20. In embodiments, the magnetic particles are formed in the absence of a polymerization reaction.

EXAMPLES

Additional aspects of the magnetic particles and their synthesis are disclosed in the following non-limiting examples.

Example 1

Synthesis of Carboxylate Anion Encapsulated MNPs from Poly(Ethylene-Alt-Maleic Anhydride) (PEMA-$Fe_3O_4$).

PEMA powder (0.6 g, MW=100,000-500,000) was dispersed with 100 mL deionized water in a 1 L-reaction vessel. Then 250 mL of $FeSO_4.7H_2O$ solution (10.5 g) was added into the reaction vessel with vigorous stirring under nitrogen atmosphere, followed by the addition of 80 mL of 2 M $KNO_3$. The reaction vessel was heated to 30° C. with vigorous stirring and nitrogen purging. When the temperature reached 30° C., 150 mL of 1 M NaOH was added drop-wise. Following the NaOH addition, the solution was heated to 90° C. and maintained at 90° C. for 2 hours.

The heat source was then turned off and the solution was cooled naturally to 25° C. PEMA-encapsulated $Fe_3O_4$ nanoparticles were collected from the solution using a magnet and washed with deionized water. The nanoparticles were re-dispersed in deionized water and stored at 25° C.

Figure 13:
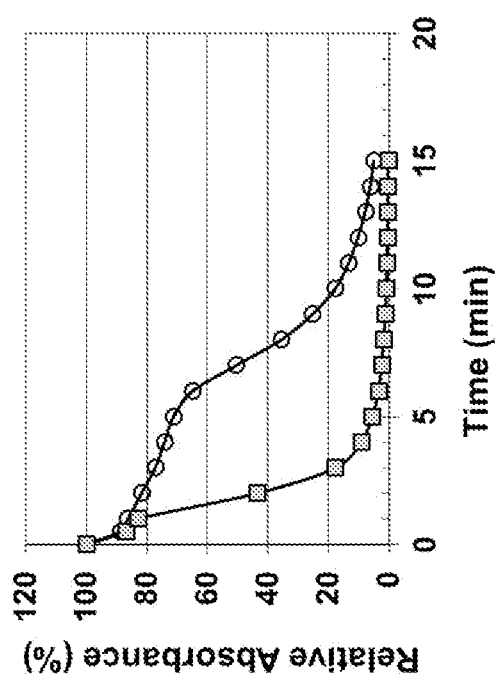
FIG. 13 is a graph illustrating response times, as displayed by relative absorbance over time data for PEMA-$Fe_3O_4$ nanoparticles (open squares) and for commercially-available magnetic beads (open circles).
Figure 14:
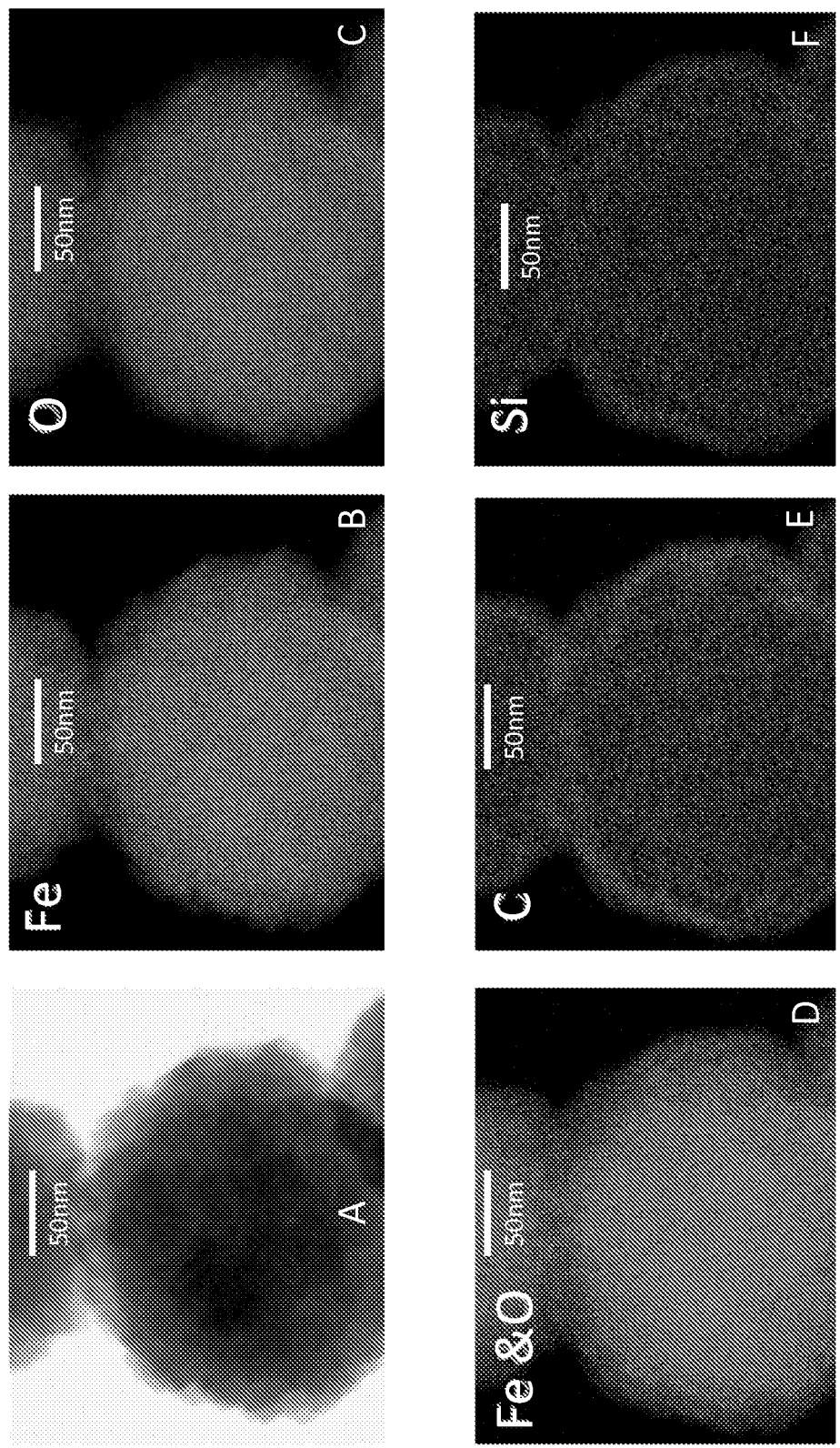
FIG. 14 A-F are STEM micrographs of PEMA-encapsulated $Fe_3O_4$ particles, illustrating the location of elements including Fe, O, C and Si.

Shown in FIG. 13 are response times, as displayed by relative absorbance over time data for PEMA-$Fe_3O_4$ nanoparticles (open squares). Also shown in FIG. 13 are data for commercially-available magnetic beads (open circles).

Example 2

Synthesis of Imino and Amino Group Encapsulated MNPs from Polyethyleneimine (PEI-$Fe_3O_4$).

In this example, 5.2 g of $FeSO_4.7H_2O$ was dissolved in 320 mL of deionized water followed by the addition of 40 mL of 2 M $KNO_3$ and the drop-wise addition of 40 mL of 1 M NaOH under a nitrogen atmosphere with vigorous stirring. Following the NaOH addition, 200 mL of 4 g/L PEI (MW=600-60,000) solution was added to the reaction vessel and the solution was heated to 90° C. and maintained at 90° C. for 2 hours.

The heat source was then turned off and the solution was cooled naturally to 25° C. PEI-encapsulated $Fe_3O_4$ nanoparticles were collected from the solution using a magnet and washed with deionized water. The nanoparticles were re-dispersed in deionized water and stored at 25° C.

In embodiments, the size and morphology of the PEI-$Fe_3O_4$ particles were controlled by varying the molecular weight of the polymer and/or the iron:polymer mass ratio. In embodiments, the mass ratio of iron to polymer (e.g., Fe:PEI) may range from 1:0.25 to 1:4, e.g., 1:0.25, 1:0.33, 1:0.5, 1:1, 1:2, 1:3 or 1:4, including ranges between any of the foregoing.

FIG. 14A-F are STEM micrographs showing the composition and structure of PEI-$Fe_3O_4$ particles. Scanning Transmission Electron Microscopy (STEM) is technique that images a sample using an electron beam. Image resolutions that are around 1-2 Å are provided by high energy electrons, which are incident on ultra-thin samples. Not only obtain exceptional image resolution, it is additionally possible to characterize crystallographic phase, crystallographic orientation (using diffraction mode experiments), generate elemental maps (by using EDS or EELS), and acquire images highlighting elemental contrast (dark field mode). These can all be accomplished from precisely located nm sized areas. The samples were prepared by dropping cast of ethyl alcohol suspension of carbon supported nanoparticles onto a carbon-coated copper grid followed by solvent evaporation at room temperature. The measurements were performed on FEI Titan G2 80-200 Chemi-STEM electron microscope at 200 kV. While not visible in black and white patent figures, these studies indicate that elemental silicon and carbon sit outside the magnetic core.

Figure 15:
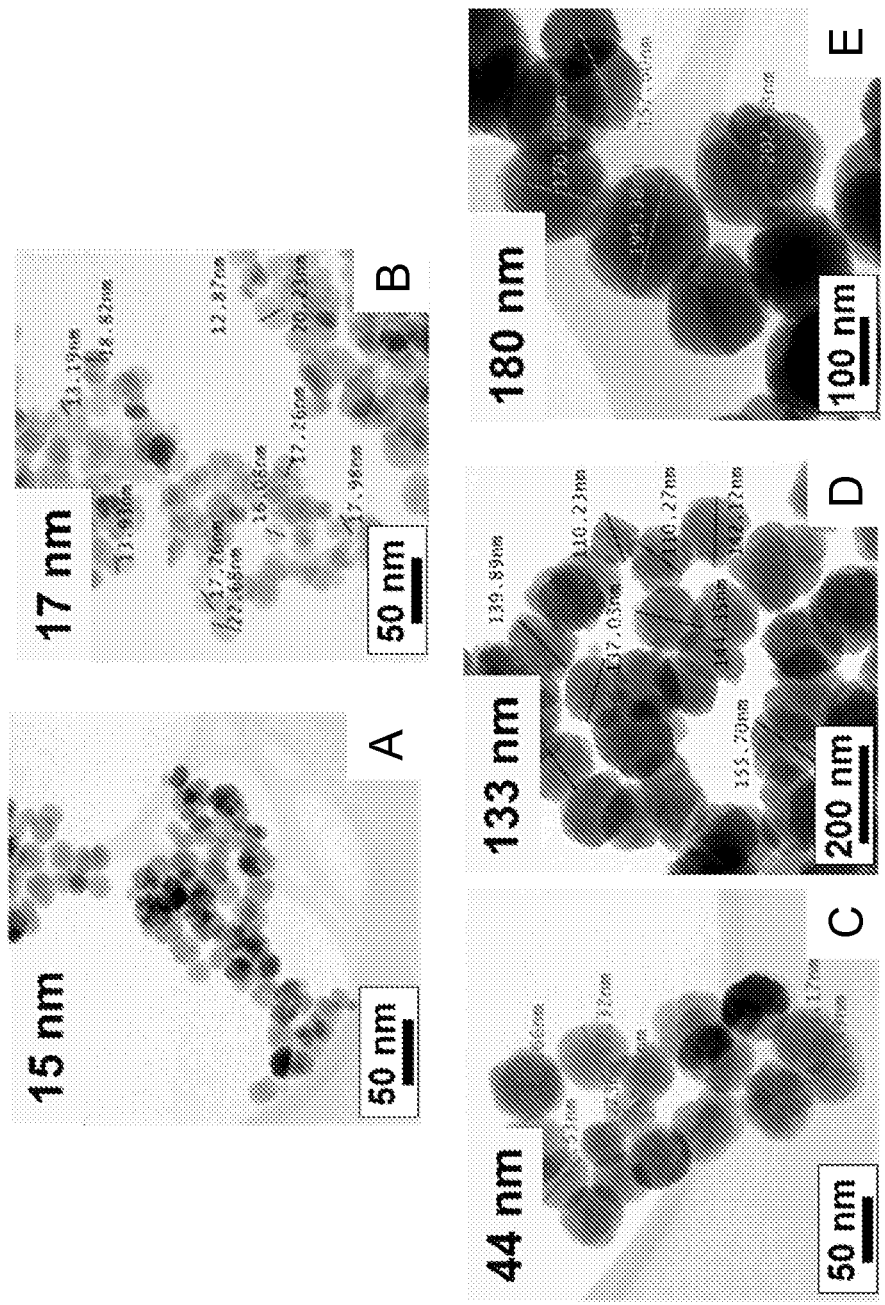
FIG. 15A-E are TEM micrographs of PEI-encapsulated $Fe_3O_4$ particles.

The size and morphology of the particles are shown in the SEM images of FIG. 15 A-E. The average particle size, molecular weight of the polymer, and mass ratio of iron to polymer for various PEI-$Fe_3O_4$ particles, are summarized in Table 3 for samples A-E.

TABLE 4

| Sample | Average size (nm) | MW | Fe:PEI |
| --- | --- | --- | --- |
| A | 15 | 600 | 1:0.77 |
| B | 17 | 1800 | 1:1.52 |
| C | 44 | 1800 | 1:0.76 |
| D | 133 | 25000 | 1:0.47 |
| E | 180 | 1800 | 1:0.38 |

Example 3

Synthesis of Carboxylate with Hydrophobic Group-Encapsulated MNPs from Poly(Methacrylic Acid, Sodium Salt) Solution (PMAA-$Fe_3O_4$).

Nanoparticles were synthesized from a poly(methacrylic acid, sodium salt) solution. In the current example, 10.5 g of $FeSO_4.7H_2O$ was dissolved in 300 mL of deionized water in a 1 L reaction vessel, followed by the addition of 80 mL of 2 M $KNO_3$ and the drop-wise addition of 80 mL of 1 M NaOH under the nitrogen atmosphere with vigorous stirring. The reaction vessel was heated up to 50° C. with vigorous stirring.

When the temperature reached 50° C., 22 mL of 3.4 wt. % PMAA (MW=9,500) aqueous solution was added to the reaction vessel. The mixture was then heated to 90° C. and maintained at 90° C. for 2 hours.

The heat source was then turned off and the solution was cooled naturally to 25° C. PMMA-encapsulated $Fe_3O_4$ nanoparticles were collected from the solution using a magnet and washed with deionized water. The nanoparticles were re-dispersed in deionized water and stored at 25° C.

Example 4

Synthesis of Carboxylate with Sulfonic Group-Encapsulated MNPs from Poly(4-Styrenesulfonic Acid-Co-Maleic Acid) Sodium Salt Solution (PSSMA-$Fe_3O_4$).

In this example, 21 g $FeSO_4.7H_2O$ was dissolved in 300 ml of distilled water in a 1 L-reaction vessel followed by the addition of 160 ml of 2.0M $KNO_3$ and the drop-wise addition of 120 mL of 2M NaOH solution under a nitrogen atmosphere with vigorous stirring. The reaction vessel was heated to 50° C. with vigorous stirring.

When the temperature reached 50° C., 5 mL of 25% PSSMA (MW=20,000) was added drop-wise into the reaction vessel under a nitrogen purge and vigorously stirring. The mixture was then heated to 90° C. and maintained at 90° C. 2 hours.

The heat source was then turned off and the solution was cooled naturally to 25° C. PSSMA-encapsulated $Fe_3O_4$ nanoparticles were collected from the solution using a magnet and washed with deionized water. The nanoparticles were re-dispersed in deionized water and stored at 25° C.

Example 5

Superconducting Quantum Interference Device (SQUID) Magnetometry

Magnetic measurements on dried powder samples were performed using a SQUID magnetometer (Quantum Design MPMS XL-5). The magnetization (M) was measured at 298K (room temperature) under an applied magnetic field (H) by cycling the field over the range −50,000 Oe to 50,000 Oe. The saturation magnetization, coercivity, and magnetic remanence for MNPs samples (Example 1-4) are plotted in FIG. 9 and FIG. 10. A summary of the particle size, magnetization, and coercivity ($H_c$) for select nanoparticle materials are summarized in Table 2, which shows collective behaviors of superspin glass magnetism due to strong inter-particle interactions. Temperature dependence vs. magnetic moment at a low field was measured by zero field cool and field cool mode. First make field zero then cool the sample to required temperature at 2K and apply a low field about 1 oe, then start taking measurement in warming mode to over room temperature (300-350K). After ZFC, kept the field while cooling temperature to 2K with the measurement and record magnetic moment of samples. FIG. 5 and FIG. 6 are temperature dependence vs. magnetic moment of PEMA-$Fe_3O_4$ and PEI-$Fe_3O_4$, respectively. Both of MNPs magnetic moment value trends in the temperature of 2-300K and 2-350K cannot be fitted into conventional magnetism, as well most of supperparamagnetic magnetite. In the FIG. 5 and FIG. 6, they show a similar increasing trend with temperature raise. There is no indication that a maximum had been reached in the experimental temperature range, which indicates the blocking temperatures ($T_B$) for all samples are well above 300 K.

Example 6

Composition and Crystalline Structure of MNP

The composition and crystalline structure of the magnetic particles was assessed using an X-ray powder diffraction (XRD) instrument and the results are reported in FIG. 7. XRD result showed all MNPs are $Fe_3O_4$ with inverse cubic spinel crystalline structure. That is, all of the crystals were the same phase.

Example 7

Surface Charge Evaluation of Polymer Encapsulated MNPs

The presence of surface charge groups such as carboxyl groups on the magnetic particles was assessed using the toluidine blue O (TBO) technique. The method includes buffer preparation, staining, and measurement.

A pH=11 buffer comprises 100 mL of 0.2M NaCl mixed with 26 mL of 0.2M HCl. A pH=2 buffer comprises 100 mL of 0.05M $NaHCO_3$ mixed with 45 mL of 0.1M NaOH. A toluidine blue O staining solution comprises toluidine blue O (TBO) (Sigma Aldrich) powder dissolved in the pH=11 buffer at a concentration of 0.05%.

In the staining and measurement steps, a 20 μl or 50 μl suspension of magnetic particles or control beads was added to a 2.0 ml Axygen tube. The tube was placed in a 12 tube IMAG magnetic separation device. The particles were drawn to the side of the tube, the clear supernatant was removed, and 1 ml of water was added to the tube. The tube was then taken out of the separation device and centrifuged to re-suspend the particles. The tube was then returned to the separation device. After the particles settled, the clear supernatant was removed and 0.5 ml of 0.05% TBO staining solution was added to the tube and centrifuged to re-suspend the particles for staining. After staining, the particles were washed 3 times with water using the standard washing process described above. After washing, 1 ml of the pH=2 buffer was added to elute the bound dye. After elution, the tube was returned to the magnetic separation device. After settling of the particles, the supernatant was taken for OD measurement at 630 nm.

Figures 16, 17:
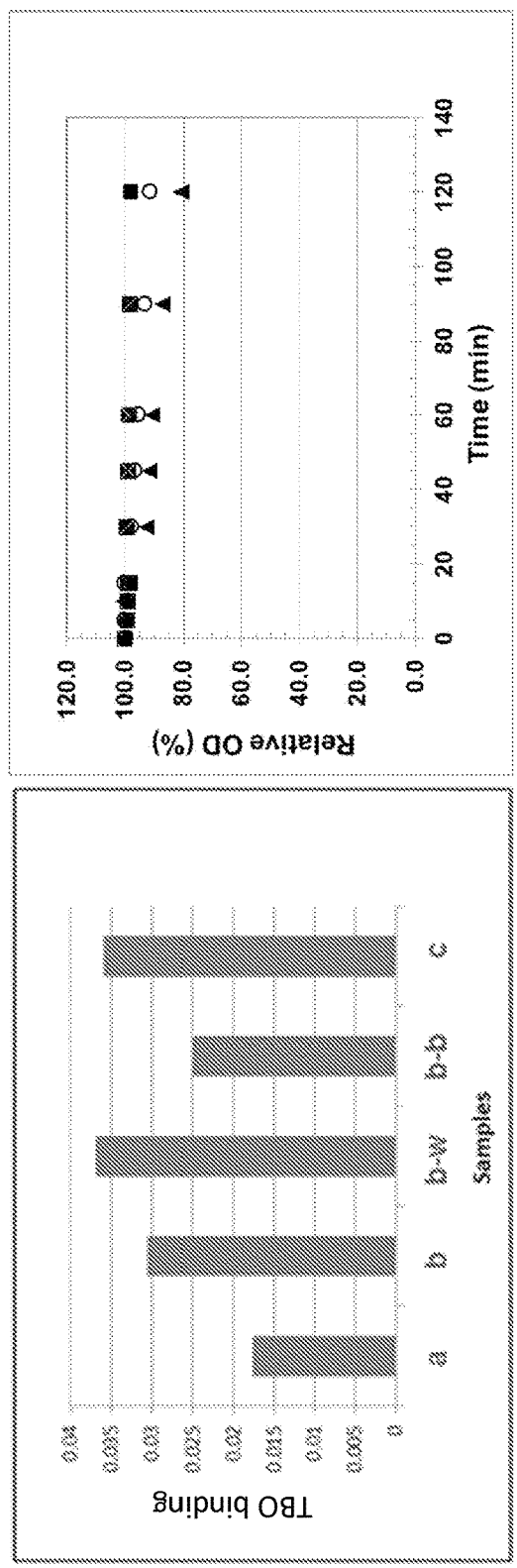
FIG. 16 is a plot characterizing the surface charge of example magnetic particle.
FIG. 17 is a plot of relative optical density (OD) versus time for suspended magnetic particles.

TBO concentrations ranging from 1 μg/ml to 10 μg/ml in the pH=2 buffer were used to create a standard curve for the calculation of the dye concentration in the final elution solution. FIG. 16 is the surface charge characterization of select polymer-encapsulated MNPs, as shown in Table 5 using TBO technology. TBO binding (on the Y axis) is measured in mg/mg magnetic NP. and FIG. 17 is a plot of relative optical density versus suspension time in the water solution, showing a decrease in the concentration of suspended particles in the solution. The PEMA-$Fe_3O_4$ (50-100 nm) magnetic particles (sample b in Table 5, shown by the circles in FIG. 17) and the PMMA-$Fe_3O_4$ (40-60 nm) magnetic particles (sample c in Table 4, shown by the triangle in FIG. 17) remain at least 80% suspended after 2 hr, which compares favorably with the commercially-available, micron-scale (10-20 wt. % magnetic phase) beads, shown by the square in FIG. 17.

TABLE 5

| Sample | Description |
|---|---|
| a | PEMA-$Fe_3O_4$ (180-250 nm) |
| b | PEMA-$Fe_3O_4$ (50-100 nm) |
| b-w | Sample b in water |
| b-b | Sample b in buffer (40% polyol 4290, 2M NaCl, 1x Tris-EDTA) |
| c | PMMA-$Fe_3O_4$ (40-60 nm) |
| comm | commercial magnetic beads |

Example 8

Isolation of DNA from Whole Blood

PEMA-$Fe_3O_4$ and PEI-$Fe_3O_4$ particles were used to isolate DNA from whole blood. 40 μl of magnetic particles (at 10 mg/mL stock concentration), 15 mL of lysis buffer, and then 5 mL of whole blood was added to a conical tube, and inverted to mix. Then the mixture was mixed on a rocker at room temperature for 5 minutes on medium speed. The tube was then placed on a 50 mL magnetic separator for 3 minutes to allow the magnetic particles to completely adhere to the side of the conical tube. Supernatant was removed and 5 mL of lysis buffer was added. The tube was gently inverted 3 times by hand. The tube was incubated for 1 minute. Then the tube was placed on the magnetic separator again for 1 minute. Supernatant was again removed. A pellet containing magnetic beads with lysed cell contents remained in the tube. To purify DNA, 20 μl of proteinase K solution was added to the tube and vortexed, then incubated at 60° C. for 10 minutes. The solution was allowed to cool to room temperature for 5-10 minutes. Then 3 mL of 100% IPA and 3 mL of protease buffer was added to the mixture. The mixture was then gently swirled by hand. A pellet containing magnetic particles containing DNA formed. Then the tube was placed on the magnetic separator for 2 minutes. The supernatant was removed. To wash, 2 mL of wash buffer 1 was added, swirled by hand for 30 seconds, the tube was placed on the magnetic separator for 1 minute, and the supernatant was again removed. A second was step was performed by adding 1 mL of wash buffer 2 to the tube, incubating at room temperature for 1 minute, and then the supernatant was removed.

Figure 18:
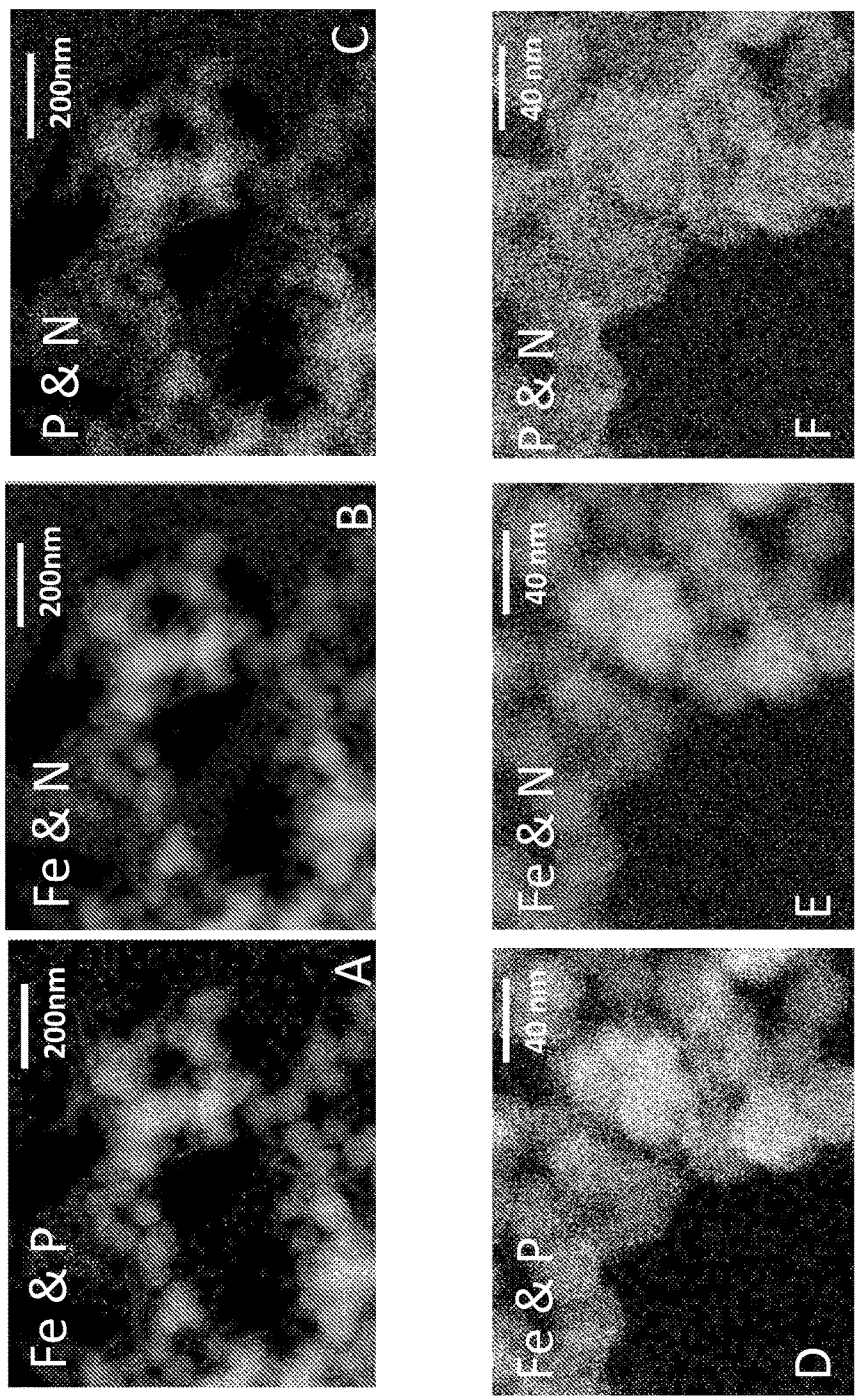
FIG. 18 shows hypermap of elements spectral images of example magnetic nanoparticles without and with DNA bound on the surface.

Hypermap spectra imaging carbon, iron, oxygen, nitrogen and phosphorus before (FIGS. 18 A, B and C) and after (D, E and F) DNA binding to PEI-Fe3O4 particles are shown in FIG. 18. As can be seen in FIG. 18, N and P were present after DNA binding to MNP. Measurements were taken at HV 200.0 kV.

To remove DNA from the magnetic particles, 1 mL of elution buffer was added to the tube, and was incubated at 60° C. for 15 minutes. Supernatant containing purified DNA was then removed and placed in a clean 1.7 mL DNase-free microcentrifuge tube. Using these methods, a yield of 160-180 μg of gDNA was obtained from 5 mL of cow whole blood with a purity ($A_{260}/A_{280}$)=~2.2.

Figure 19:
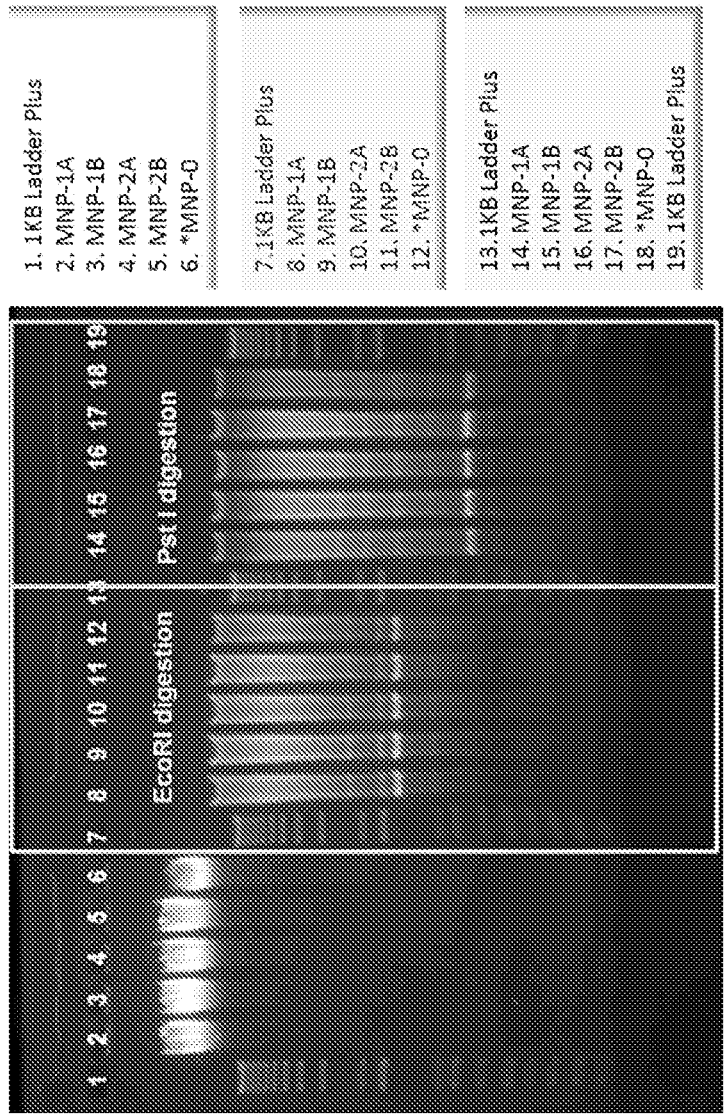
FIG. 19 is a digital image of gel electrophoresis result confirming DNA purification using magnetic nanoparticles.

FIG. 19 illustrates the application of MNPs to the genomic DNA purification from whole blood using PEMA-$Fe_3O_4$. DNA was run on a 1% agarose gel in 1×TBE buffer. FIG. 19 is a digital image of the stained gel for supercoiled genomic DNA (lanes 2-6), genomic DNA fragments resulting from Eco R1 restriction enzyme digestion (lanes 8-13), and genomic DNA fragments resulting from Pst I restriction enzyme digestion (lanes 14-18). All digestions were done for 4 hours at 37° C. MNP-1 and MNP-2 represent 2 different batches using the same PEMA-$Fe_3O_4$ from separate syntheses, and A and B represent replicate genomic DNA isolations from whole blood. *MNP-0 represents genomic DNA isolated from whole blood that was stored at −20° C. for 18 months, showing the stability of the isolated genomic DNA.

Example 9

Isolation of DNA from PCR (PCR Clean-Up)

MNPs were provided at 10 mg/mL in water. 10 mL of MNPs were vortexed and then resuspended in 13.3 mL of Corning DNA binding buffer to reach a final concentration of 7.5 mg/mL. 20 µl of MNPs were dispensed into individual wells of a PCR plate. The PCR product to be purified was gently vortexed and 20 µl of the PCR product was dispensed into each well already containing 20 µl of the MNP suspension. The solution was pipetted to mix about 10 times. The mixture was incubated at RT for 5 minutes to allow DNA to bind to the MNPs. The PCR plate was placed in an IMAG96P magnet separation device (available from Axygen, Foster City, Calif.). the supernatant was then removed. The DNA bound particles were then washed in 150 µl of 70% ethanol, allowing the ethanol wash to incubate of 30 seconds. The ethanol was removed. This ethanol wash step was repeated. The PCR plate was allowed to stay on the IMAG96P device while the plate was allowed to dry at room temperature. Then 40 µl of elution buffer or water was added to each well and incubated at room temperature for 30 seconds. The solution was then mixed to resuspend the magnetic particles. The PCR plate was then placed back onto the IMAG96P device to capture the MNPs until the supernatant appeared clear. The supernatant containing PCR product was then removed.

Figures 20, 21:
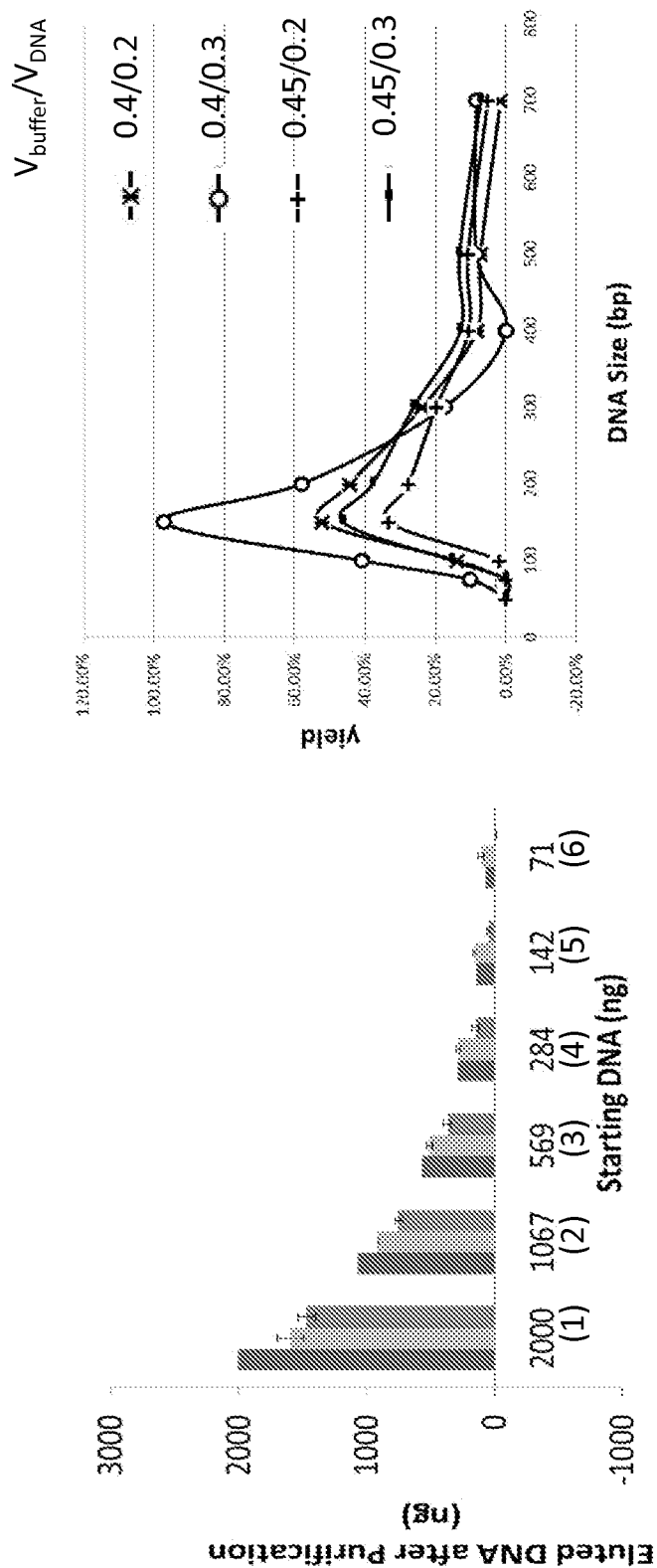
FIG. 20 is a plot showing the DNA binding capacity of example magnetic nanoparticles; and, FIG. 21 is a graph illustrating data for DNA size selection yielded using embodiments of MNP.

Illustrated in FIG. 20 is (A) the DNA binding capacity of MNP in a PCR cleanup assay. For each of the six illustrated assays (1)-(6), the left-most candle represents the starting DNA concentration, the middle candle represent data for the disclosed MNPs, and the right-most candle represents data from a commercial kit. Comparing the amount of eluted DNA after purification, the disclosed MNP material consistently outperforms the commercial product with yields of 80-90%. The PCR cleanup assay is based on 2 microliters of starting DNA material, 40 microliters of elution buffer, and 20 microliters of 7.5 mg/mL magnetic nanoparticles.

With reference to FIG. 21, by varying the $V_{DNA}$ versus $V_{buffer}$+MNP ratio, it is possible to selectively purify DNA within a specific size range. As used herein, 0.4/0.2, for example, means that 1 part of DNA solution is first added to 0.4 part of magnetic particles in binding buffer to remove the largest size DNA. The supernatant is then combined with 0.2 part of magnetic particles in binding buffer to bind the targeted DNA to the particles and leave the smaller size DNA and contamination in the supernatant. The size of the PCR product is 538 bp.

The magnetic particles disclosed herein may be used in bioprocessing, such as for the separation, isolation and/or purification of cells, cell components, or cellular products, including antibodies, viruses, proteins, drugs, etc. By way of example, the magnetic particles may be used for the separation, isolation and/or purification of endosomes, membrane fractions, mitochondria, ribosomes, sub cellular organelles, etc.

As a further example, the magnetic particles may be used for the purification of nucleic acids, including cell-free fetal DNA, PCR product DNA, genomic DNA, mRNA, total RNA, microRNA, viral RNA or DNA, bacterial RNA or DNA, plasmid DNA, etc. Nucleic acids, as well as peptides and proteins, may be derived from a variety of biological sources, such as whole blood, plasma, serum, buffy coat, bone marrow, amniotic fluid, spinal fluid, other bodily fluids (e.g., saliva, nasal, cheek, vaginal or throat swabs), hair follicles, stool, urine, tissue, fresh or frozen samples, formalin-fixed paraffin-embedded (FFPE) samples, and plant samples.

Nucleic acids purified with particulate magnetic material can be used for various applications, such as (non-invasive) prenatal screening, cancer testing, virus or bacteria detection/diagnostics, blood donor screening, organ donor matching, genetic disease studies for inherited disorders, genealogical testing, ethnicity testing, human leukemia antigen (HLA) testing, agriculture, or genetic/genomic/epigenomic research. Peptides or proteins adsorbed to the surface of a magnetic particle may be used as targeting molecules for ELISA or chemiluminescence assays.

As used herein, the singular forms "a," "an" and "the" include plural referents unless the context clearly dictates otherwise. Thus, for example, reference to a "magnetic particle" includes examples having two or more such "magnetic particles" unless the context clearly indicates otherwise The term "include" or "includes" means encompassing but not limited to, that is, inclusive and not exclusive.

"Optional" or "optionally" means that the subsequently described event, circumstance, or component, can or cannot occur, and that the description includes instances where the event, circumstance, or component, occurs and instances where it does not.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It is also noted that recitations herein refer to a component being "configured" or "adapted to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a nanoparticle comprising a magnetic core and a polymer shell include embodiments where a nanoparticle consists of a magnetic core and a polymer shell and embodiments where a nanoparticle consists essentially of a magnetic core and a polymer shell.

It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

We claim:

1. Magnetic particles comprising:
a magnetic core and a polymer coating;
wherein the magnetic core comprises a metal, metal alloy, or metal oxide of at least one metal selected from the group consisting of B, Mg, Al, Mn, Co, Ni, Cu, Fe, Nb, Sm, La, Yb, Dy, Gd or Er;
wherein the magnetic core comprises polycrystalline particles which are superparamagnetic and which are coalesced to form a superspin glass magnetic core;
wherein the polymer coating surrounds the magnetic core;
and wherein the magnetic particles exhibit coercivity greater than zero and less than 300 Oe and magnetic remanence between 3 and 10 emu/g at room temperature;
wherein the magnetic particle has a particle size of 500 nm or less.

2. The magnetic particles of claim 1 wherein the polycrystalline particles of the magnetic core are the same crystalline phase.

3. The magnetic particles of claim 1, wherein the particles comprise a saturation magnetization greater than 50 and less than 100 emu/g at room temperature.

4. The magnetic particles of claim 1, wherein the polycrystalline particles which have coalesced to form a superspin glass magnetic core is a soft a soft magnetic material.

5. The magnetic particles of claim 1, wherein the coercivity is between 30 and 150 Oe.

6. The magnetic particles of claim 1, wherein the polymer coating is selected from the group consisting of poly(ethyl methacrylate), poly(ethylene-alt-maleic anhydride), poly(methyl methacrylate), polyethyl imine, poly(methacrylic acid), poly(4-styrene sulfonic acid-co-maleic acid), polyacrylic acid, polyvinyl alcohol, poly thiol, and poly mercapto acid or a combination.

7. The magnetic particles of claim 1, wherein the core comprises at least 60 wt. % of the particle.

8. The magnetic particles of claim 1, wherein the magnetic particle has a diameter of 10 to 250 nm.

9. The magnetic particles of claim 1, wherein the polymer coating has an average thickness of between 10 nm to 250 nm.

10. The magnetic particles of claim 1 further comprising a surface functional group selected from the group consisting of carboxylic acid/carboxylate, amino/imine, methyl, methylene, thiol, anhydride, phosphoric acid, sulfuric acid/sulfonate, sulfonamide, and phosphatide.

11. The magnetic particles of claim 1, wherein the magnetic core comprises $Fe_3O_4$.

* * * * *

UNITED STATES PATENT AND TRADEMARK OFFICE
CERTIFICATE OF CORRECTION

PATENT NO. : 10,319,502 B2
APPLICATION NO. : 15/520581
DATED : June 11, 2019
INVENTOR(S) : Ann MeeJin Ferrie et al.

It is certified that error appears in the above-identified patent and that said Letters Patent is hereby corrected as shown below:

On the Title Page

Item [57], in Column 2, Line 7, delete "Fe" and insert -- Fe, --, therefor.

On page 2, item [56], Column 2, Line 21, delete ""Enhacenment" and insert -- "Enhancement --, therefor.

In the Claims

Column 20, Line 7, Claim 4, delete "a soft a soft" and insert -- a soft --, therefor.

Signed and Sealed this
Twenty-second Day of October, 2019

Andrei Iancu
*Director of the United States Patent and Trademark Office*